(12) United States Patent
Serra Miralles et al.

(10) Patent No.: US 9,086,390 B2
(45) Date of Patent: Jul. 21, 2015

(54) DABIGATRAN ETEXILATE AND RELATED SUBSTANCES, PROCESSES AND COMPOSITIONS, AND USE OF THE SUBSTANCES AS REFERENCE STANDARDS AND MARKERS

(75) Inventors: Judit Serra Miralles, Girona (ES); Ernesto Durán López, Barcelona (ES); Lingxiang Rao, Nanjing (CN)

(73) Assignee: Medichem, S.A., Sant Joan Despí (ES)

( * ) Notice: Subject to any disclaimer, the term of this patent is extended or adjusted under 35 U.S.C. 154(b) by 0 days.

(21) Appl. No.: 14/076,761

(22) PCT Filed: May 10, 2012

(86) PCT No.: PCT/EP2012/058604
§ 371 (c)(1),
(2), (4) Date: Nov. 11, 2013

(87) PCT Pub. No.: WO2012/152855
PCT Pub. Date: Nov. 15, 2012

(65) Prior Publication Data
US 2014/0076036 A1    Mar. 20, 2014

(30) Foreign Application Priority Data

May 11, 2011 (EP) ..................................... 11382139

(51) Int. Cl.
*C07D 235/14* (2006.01)
*G01N 33/00* (2006.01)
*C07D 401/12* (2006.01)

(52) U.S. Cl.
CPC .............. *G01N 33/00* (2013.01); *C07D 235/14* (2013.01); *C07D 401/12* (2013.01)

(58) Field of Classification Search
CPC ........................... C07D 235/14; C07D 401/12
See application file for complete search history.

(56) References Cited

U.S. PATENT DOCUMENTS

| 6,087,380 A | 7/2000 | Hauel et al. |
| 7,202,368 B2 | 4/2007 | Zerban et al. |

FOREIGN PATENT DOCUMENTS

| WO | WO 00/05207 A1 | 2/2000 |
| WO | WO 2007/071742 A1 | 6/2007 |
| WO | WO 2007/071743 A1 | 6/2007 |
| WO | 2010/045900 * | 4/2010 |
| WO | WO 2010/045900 A1 | 4/2010 |
| WO | WO 2011/061080 A1 | 5/2011 |

OTHER PUBLICATIONS

Chemical Abstracts Registry No. 211915-06-9, indexed in the Registry file on STN CAS Online Oct. 1, 1998.*
Hauel, J Med CHem, vol. 45, pp. 1757-1766, 2002.*
Hauel et al., "Structure-Based Design of Novel Potent Nonpeptide Thrombin Inhibitors," Journal of Medicinal Chemistry, 45(9): 1757-1766, 2002.
"CHMP Assessment Report for Pradaxa," European Medicines Agency, Document Reference: EMEA/174363/2008 (Apr. 23, 2008) 1-36.
European Patent Office, International Search Report in PCT/EP2012/058604 (Jul. 12, 2012).

* cited by examiner

*Primary Examiner* — D M Seaman
(74) *Attorney, Agent, or Firm* — Leydig, Voit & Mayer, Ltd.

(57) ABSTRACT

The present invention relates to dabigatran etexilate and related substances and use of the substances as reference standards and markers. There are also provided processes of detecting the substances in samples of dabigatran etexilate, or pharmaceutically acceptable salts or solvates thereof, and also for analyzing the purity of samples of dabigatran etexilate, or pharmaceutically acceptable salts or solvates thereof. There are still further provided processes of preparing dabigatran etexilate and related substances, and pharmaceutical compositions containing the same.

18 Claims, No Drawings

DABIGATRAN ETEXILATE AND RELATED SUBSTANCES, PROCESSES AND COMPOSITIONS, AND USE OF THE SUBSTANCES AS REFERENCE STANDARDS AND MARKERS

CROSS-REFERENCE TO RELATED APPLICATIONS

This patent application is the U.S. national phase of International Patent Application No. PCT/EP2012/058604, filed on May 10, 2012, which claims the benefit of European Patent Application No. EP 11382139.1 filed on May 11, 2011, both of which are incorporated by reference.

BACKGROUND OF THE INVENTION

The present invention relates to dabigatran etexilate and related substances and use of the substances as reference standards and markers. There are also provided processes of detecting the substances in samples of dabigatran etexilate, or pharmaceutically acceptable salts or solvates thereof, and also for assessing the purity of samples of dabigatran etexilate, or pharmaceutically acceptable salts or solvates thereof. There are still further provided processes of preparing dabigatran etexilate and related substances, and pharmaceutical compositions containing the same.

Dabigatran etexilate (a compound of formula (I)) is the international commonly accepted non-proprietary name for ethyl 3-{[(2-{[(4-{[(hexyloxy)carbonyl] carbamimidoyl}phenyl)amino]methyl}-1-methyl-1H-benzimidazol-5-yl)carbonyl](pyridin-2-yl)amino}propanoate, which has an empirical formula of $C_{34}H_{41}N_7O_5$ and a molecular weight of 627.73.

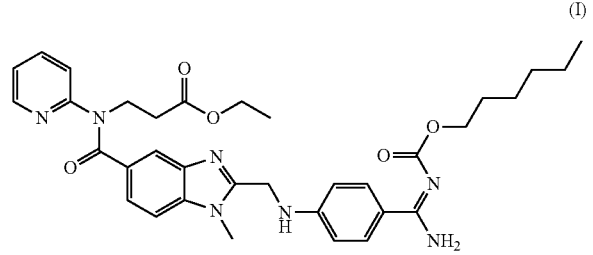 [SMILES: CCCCCCOC(=O)/N=C(/N)c1ccc(NCc2nc3cc(C(=O)N(CCC(=O)OCC)c4ccccn4)ccc3n2C)cc1]

(I)

Dabigatran etexilate is the pro-drug of the active substance, dabigatran, which has a molecular formula $C_{25}H_{25}N_7O_3$ and molecular mass 471.51. The mesylate salt (1:1) of dabigatran etexilate is known to be therapeutically useful and is commercially marketed as oral hard capsules in the United States and in Europe under the trade mark Pradaxa™ for the prevention of stroke and systemic embolism in patients with non-valvular atrial fibrillation. Additionally, it is also marketed in Europe under the same trade mark for the primary prevention of venous thromboembolic events in adult patients who have undergone elective total hip replacement surgery or total knee replacement surgery.

Dabigatran etexilate was first described in U.S. Pat. No. 6,087,380, according to which the synthesis of dabigatran etexilate was carried out in three synthetic steps (see Scheme 1). Example 58 describes the condensation between ethyl 3-{[3-amino-4-(methylamino)benzoyl](pyridin-2-yl) amino}propanoate (compound II) and N-(4-cyanophenyl) glycine (compound III) in the presence of N,N'-carbonyldiimidazole (CDI) in tetrahydrofuran to give the hydrochloride salt of ethyl 3-{[(2-{[(4-cyanophenyl)amino]methyl}-1-methyl-1H-benzimidazol-5-yl)carbonyl](pyridin-2-yl) amino}propanoate (compound IV), which is subsequently reacted with ethanolic hydrochloric acid, ethanol and ammonium carbonate to give the hydrochloride salt of ethyl 3-{[(2-[{(4-carbamimidoylphenyl)amino]methyl}-1-methyl-1H-benzimidazol-5-yl)carbonyl](pyridin-2-yl) amino}propanoate (compound V). Finally, example 113 describes the reaction between compound V and n-hexyl chloroformate (compound VI), in the presence of potassium carbonate, in a mixture of tetrahydrofuran and water, to give dabigatran etexilate after work-up and chromatographic purification. However, no information is given about the purity of the isolated dabigatran etexilate.

Scheme 1

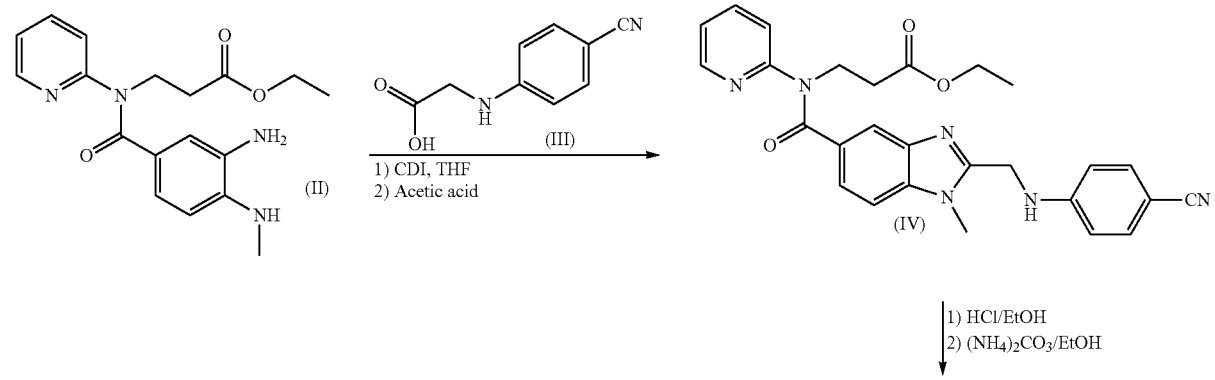

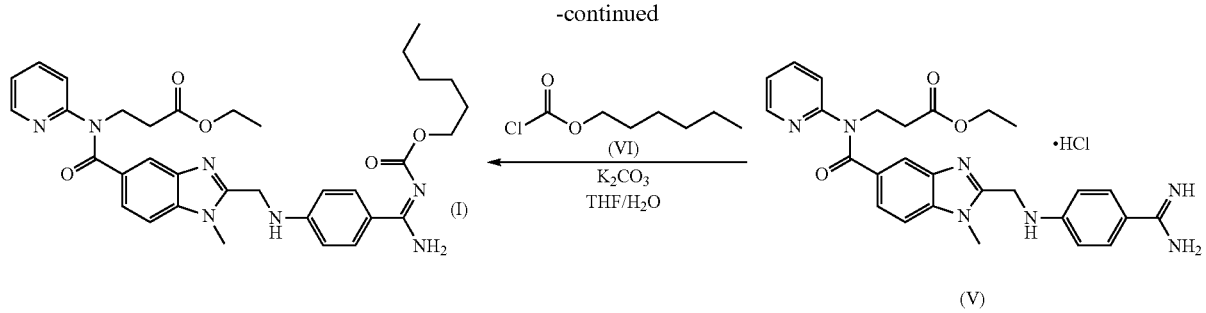

U.S. Pat. No. 7,202,368 describes an alternative process for the synthesis of dabigatran etexilate (see Scheme 2). Example 3 describes the condensation between ethyl 3-{[3-amino-4-(methylamino)benzoyl](pyridin-2-yl)amino}propanoate (compound II) and 2-[4-(1,2,4-oxadiazol-5-on-3-yl)phenylamino]acetic acid (compound VII) in the presence of a coupling agent such as N,N'-carbonyldiimidazole (CDI), propanephosphonic anhydride (PPA), or pivaloyl chloride, to give ethyl 3-{[(2-{[(4-{1,2,4-oxadiazol-5-on-3-yl}phenyl)amino]methyl}-1-methyl-1H-benzimidazol-5-yl)carbonyl](pyridin-2-yl)amino}propanoate (compound VIII), which is subsequently hydrogenated (Example 4) in the presence of a palladium catalyst to give ethyl 3-{[(2-{[(4-carbamimidoylphenyl)amino]methyl}-1-methyl-1H-benzimidazol-5-yl)carbonyl](pyridin-2-yl)amino}propanoate (compound V). Then, Example 5 describes the acylation of compound V with n-hexyl chloroformate (compound VI) to give dabigatran etexilate. Finally, Example 6 describes the conversion of dabigatran etexilate into its mesylate salt. Although the patent describes the HPLC purities of intermediate compounds II, VII, VIII and V, no information is given neither about the purity of the isolated dabigatran etexilate nor about its mesylate salt.

European Patent Applications EP 1966171A and EP 1968949A describe similar processes for the synthesis of dabigatran etexilate to that depicted in Scheme 2, but without isolating some of the intermediate compounds. HPLC purities higher than 99% are described for both dabigatran etexilate (see Examples 6B and 6C of EP 1966171A) and its mesylate salt (see Example 9 of EP 1966171A and Example 7 of EP 1968949A). However, no information is given about the structure of the impurities present in dabigatran etexilate and/or its mesylate salt.

PCT Patent Application WO 2010/045900 describes the synthesis of dabigatran etexilate mesylate with 99.5% purity by HPLC (Examples 3 and 4) by following a similar synthetic process to that described in Scheme 1. However, no information is given about the structure of the impurities present in the mesylate salt of dabigatran etexilate.

The Committee for Medicinal Products for Human use (CHMP) assessment report for Pradaxa (i.e. dabigatran etexilate mesylate salt 1:1) reference EMEA/174363/2008, as published in the European Medicines Agency website on Apr. 23, 2008, describes (page 8) that the proposed specifications for impurities in the active substance are for some specified impurities above the qualification threshold of the ICH guide- Scheme 2

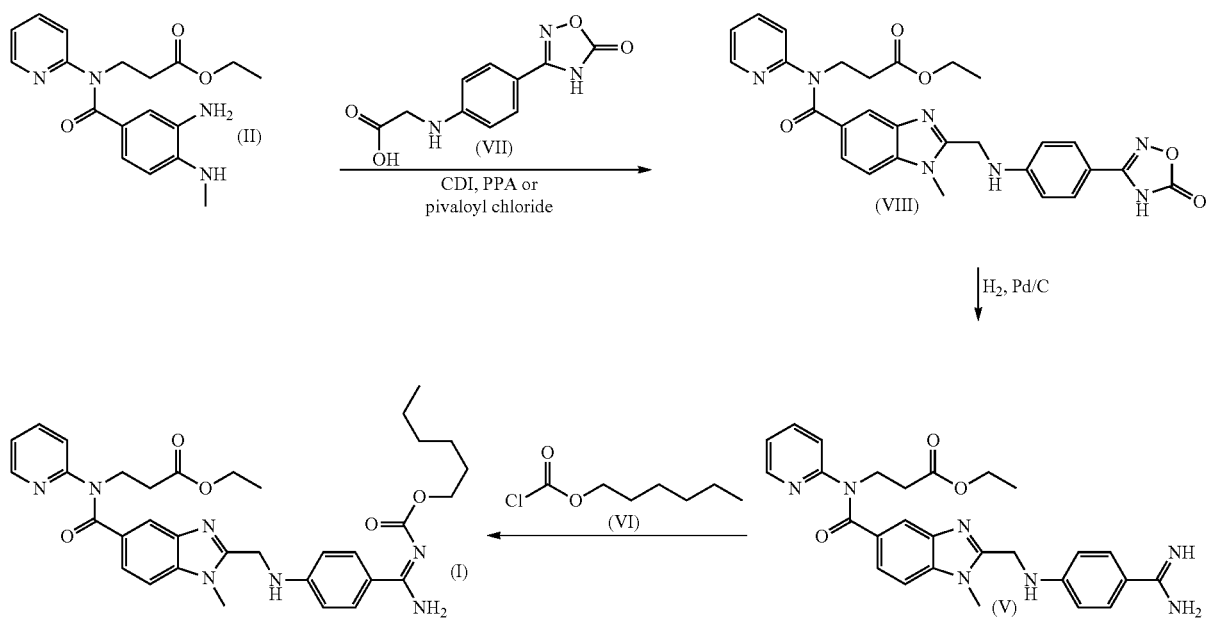

line "Impurities in new drug substances", i.e. above 0.15%. However, no information is given about the structure of the impurities present in the mesylate salt of dabigatran etexilate.

BRIEF SUMMARY OF THE INVENTION

The present invention provides a method for analyzing dabigatran etexilate, or a pharmaceutically acceptable salt or solvate thereof, and also identification of dabigatran impurities and related substances. The inventors have also appreciated that dabigatran impurities and related substances as described herein may be utilized as reference markers or reference standards for the analysis of dabigatran etexilate, or a pharmaceutically acceptable salt or solvate thereof.

DETAILED DESCRIPTION OF THE INVENTION

The terms "dabigatran impurities", "related substances" and "compounds A to D" as used herein, are used interchangeably to denote certain impurities formed in the manufacture of the API, and/or a pharmaceutical composition containing the same, and/or impurities formed by degradation of the API and/or in a pharmaceutical composition containing the same on storage.

Accordingly, a first aspect of the present invention provides a compound of formula (A)

(A)

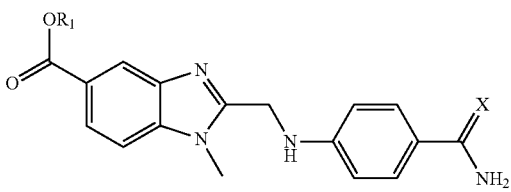

wherein $R_1$ represents $C_{1-4}$ alkyl, and X represents either NH, or $N(C=O)O(CH_2)_5CH_3$.

Preferably, formula (A) includes the following preferred sub-groups of compounds

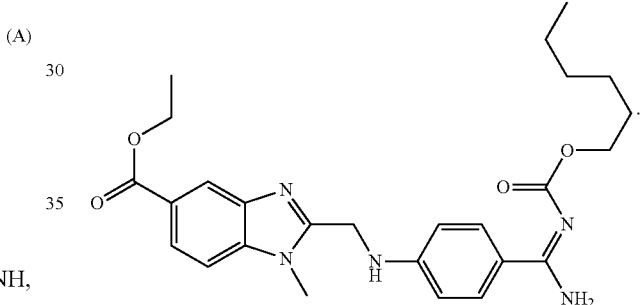

wherein $R_1$ represents $C_{1-4}$ alkyl substantially as hereinbefore described. Even more preferably in formula (A), $R_1$ represents ethyl and as such preferred individualized compounds of formula (A) are compounds (A1) and (A2) as follows.

Compound (A1) has the chemical name ethyl 2-{[(4-{carbamimidoyl}phenyl)amino]methyl}-1-methyl-1H-benzimidazol-5-carboxylate and structure (A1)

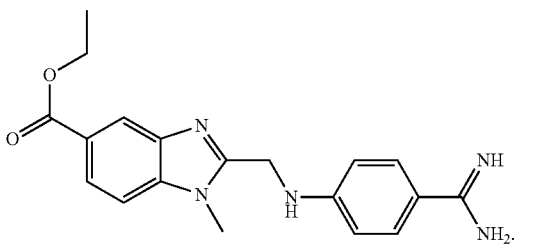

Compound (A1) can be further characterized by an empirical formula of $C_{19}H_{21}N_5O_2$, a molecular weight of 351.40, and an approximate retention time by HPLC (according to method 1 substantially as hereinafter described) of 3.5 minutes.

Compound (A2) has the chemical name ethyl 2-{[(4-{[(hexyloxy)carbonyl]carbamimidoyl}phenyl)amino]methyl}-1-methyl-1H-benzimidazol-5-carboxylate and structure (A2)

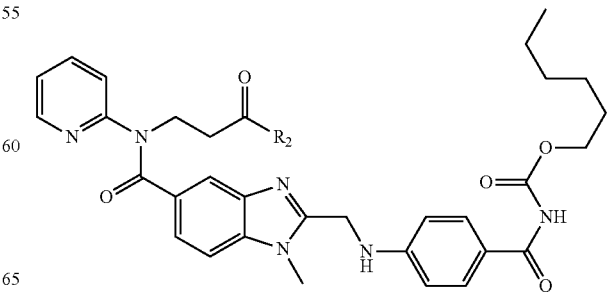

In a particular embodiment, compound (A2) is in isolated form. Preferably, the isolated form is in substantially pure form, preferably having a purity of greater than about 90%, preferably greater than about 95%, preferably greater than about 98%, most preferably greater than about 99%, preferably as measured by HPLC.

Compound (A2) can be further characterized by an empirical formula of $C_{26}H_{33}N_5O_4$, a molecular weight of 479.57, and an approximate retention time by HPLC (according to method 1 substantially as hereinafter described) of 10.4 minutes.

A second aspect of the present invention provides a compound of formula (B)

(B)

wherein $R_2$ represents a hydroxyl, $C_{1-4}$ alkoxy or $NH_2$, preferably anyone of hydroxyl, methoxy, ethoxy or $NH_2$.

Preferred individualized compounds of formula (B) are compounds (B1), (B2), (B3) and (B4) as follows.

Compound (B1) has the chemical name 3-{[(2-{[(4-{[({hexyloxy}carbonyl)amino]carbonyl}phenyl)amino]methyl}-1-methyl-1H-benzimidazol-5-yl)carbonyl](pyridin-2-yl)amino}propanoic acid and structure

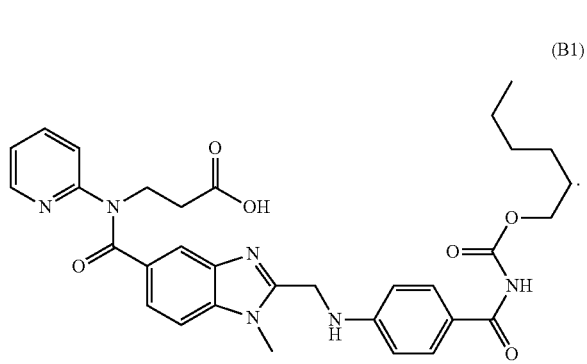 [SMILES: CCCCCCOC(=O)NC(=O)c1ccc(NCc2nc3cc(C(=O)N(CCC(=O)O)c4ccccn4)ccc3n2C)cc1]

(B1)

In a particular embodiment, compound (B1) is in isolated form. Preferably, the isolated form is in substantially pure form, preferably having a purity of greater than about 90%, preferably greater than about 95%, preferably greater than about 98%, most preferably greater than about 99%, preferably as measured by HPLC.

Compound (B1) can be further characterized by an empirical formula of $C_{32}H_{36}N_6O_6$, a molecular weight of 600.67, and an approximate retention time by HPLC (according to method 1 substantially as hereinafter described) of 7.7 minutes.

Compound (B2) has the chemical name methyl 3-{[(2-{[(4-{[({hexyloxy}carbonyl)amino]carbonyl}phenyl)amino]methyl}-1-methyl-1H-benzimidazol-5-yl)carbonyl](pyridin-2-yl)amino}propanoate and structure

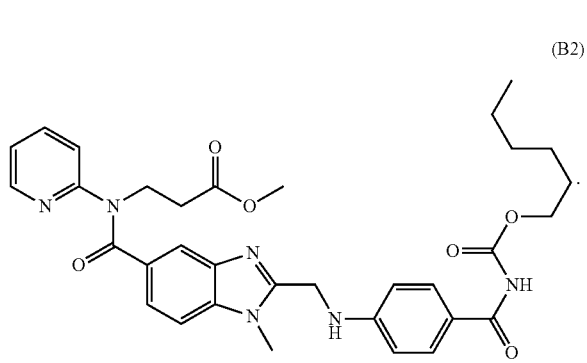 [SMILES: CCCCCCOC(=O)NC(=O)c1ccc(NCc2nc3cc(C(=O)N(CCC(=O)OC)c4ccccn4)ccc3n2C)cc1]

(B2)

Compound (B2) can be further characterized by an empirical formula of $C_{33}H_{38}N_6O_6$, a molecular weight of 614.69, and an approximate retention time by HPLC (according to method 1 substantially as hereinafter described) of 14.8 minutes.

Compound (B3) has the chemical name ethyl 3-{[(2-{[(4-{[({hexyloxy}carbonyl)amino]carbonyl}phenyl)amino]methyl}-1-methyl-1H-benzimidazol-5-yl)carbonyl](pyridin-2-yl)amino}propanoate and structure

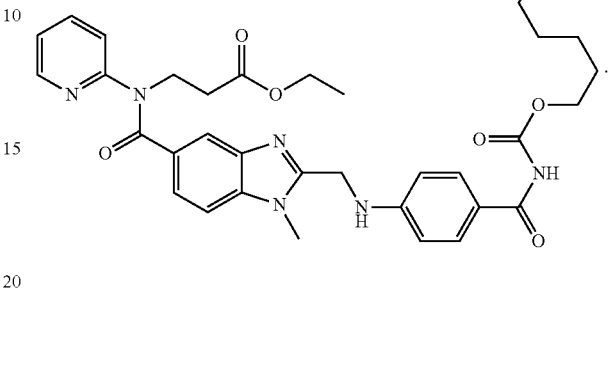

(B3)

In a particular embodiment, compound (B3) is in isolated form. Preferably, the isolated form is in substantially pure form, preferably having a purity of greater than about 90%, preferably greater than about 95%, preferably greater than about 98%, most preferably greater than about 99%, preferably as measured by HPLC.

Compound (B3) can be further characterized by an empirical formula of $C_{34}H_{40}N_6O_6$, a molecular weight of 628.72, and an approximate retention time by HPLC (according to method 1 substantially as hereinafter described) of 16.6 minutes.

Compound (B4) has the chemical name 3-{[(2-{[(4-{[(hexyloxy)carbonyl]carbamimidoyl}phenyl)amino]methyl}-1-methyl-1H-benzimidazol-5-yl)carbonyl](pyridin-2-yl)amino}propanamide and structure

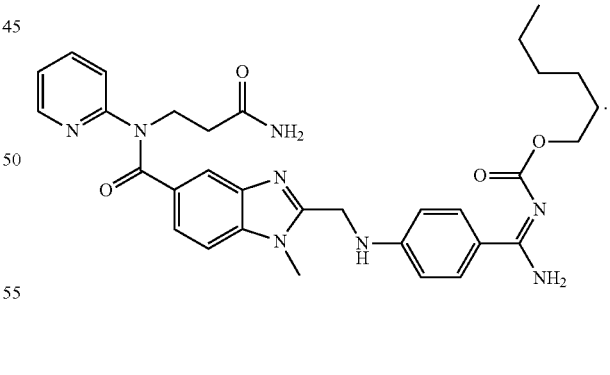

(B4)

Compound (B4) can be further characterized by an empirical formula of $C_{32}H_{38}N_8O_4$, a molecular weight of 598.70, and an approximate retention time by HPLC (according to method 1 substantially as hereinafter described) of 4.0 minutes.

A third aspect of the present invention provides a compound of formula (C) obtained by a process of preparing dabigatran etexilate and/or its salts and/or its solvates

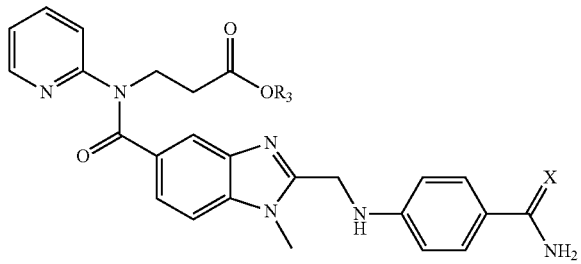
(C)

wherein $R_3$ represents hydrogen or $C_{1-4}$ alkyl, preferably hydrogen or methyl, and X represents either NH, or N(C=O)O(CH$_2$)$_5$CH$_3$.

Preferably, formula (C) includes the following preferred sub-groups of compounds

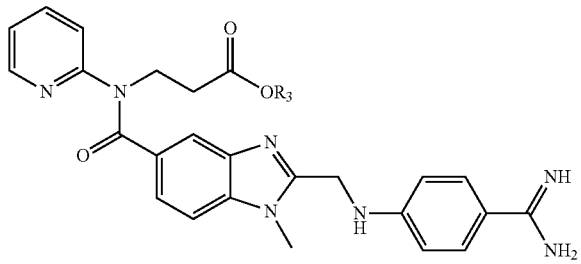

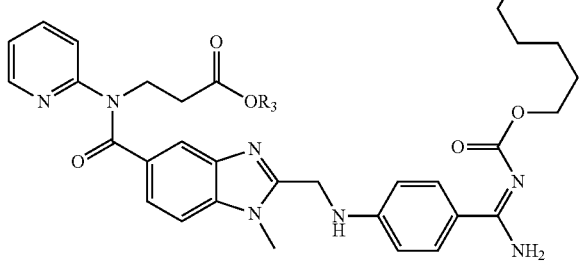

wherein $R_3$ represents hydrogen or $C_{1-4}$ alkyl, preferably hydrogen or methyl substantially as hereinbefore described. Preferred individualized compounds of formula (C) are compounds (C1), (C2) and (C3) as follows.

Compound (C1) has the chemical name 3-{[(2-{[(4-{carbamimidoyl}phenyl)amino]methyl}-1-methyl-1H-benzimidazol-5-yl)carbonyl](pyridin-2-yl)amino}propanoic acid and structure (C1)

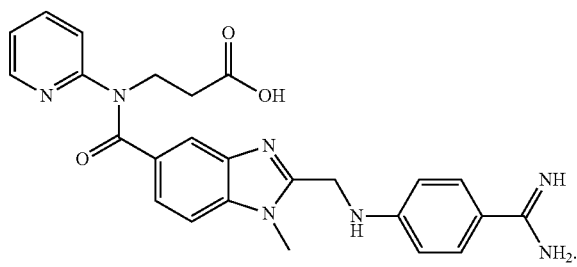

Compound (C1) is also known as dabigatran. Compound (C1) can be further characterized by an empirical formula of $C_{25}H_{25}N_7O_3$, a molecular weight of 471.51, and having an approximate retention time by HPLC (according to method 1 substantially as hereinafter described) of 2.3 minutes.

Compound (C2) has the chemical name 3-{[(2-{[(4-{[(hexyloxy)carbonyl]carbamimidoyl}phenyl)amino]methyl}-1-methyl-1H-benzimidazol-5-yl)carbonyl](pyridin-2-yl)amino}propanoic acid and structure (C2)

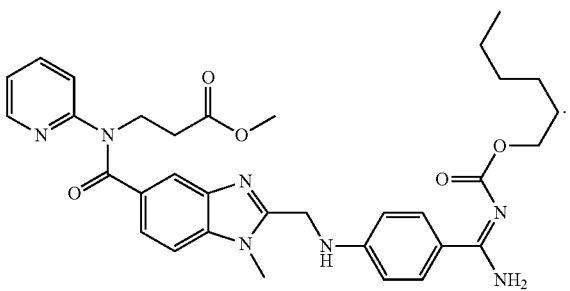

Compound (C2) can be further characterized by an empirical formula of $C_{32}H_{37}N_7O_5$, a molecular weight of 599.68, and an approximate retention time by HPLC (according to method 1 substantially as hereinafter described) of 4.5 minutes.

Compound (C3) has the chemical name methyl 3-{[(2-{[(4-{[(hexyloxy)carbonyl]carbamimidoyl}phenyl)amino]methyl}-1-methyl-1H-benzimidazol-5-yl)carbonyl](pyridin-2-yl)amino}propanoate and structure (C3)

Compound (C3) can be further characterized by an empirical formula of $C_{33}H_{39}N_7O_5$, a molecular weight of 613.71, and an approximate retention time by HPLC (according to method 1 substantially as hereinafter described) of 6.6 minutes.

A fourth aspect of the present invention provides a compound of formula (D), having the chemical name 4-{[(hexyloxy)carbonyl]carbamimidoyl}aniline and structure

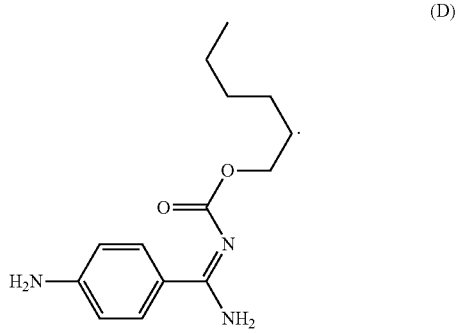 [SMILES: CCCCCCOC(=O)/N=C(/N)c1ccc(N)cc1]

Compound (D) can be further characterized by an empirical formula of $C_{14}H_{21}N_3O_2$, a molecular weight of 263.34, and an approximate retention time by HPLC (according to method 1 substantially as hereinafter described) of 5.0 minutes.

Compounds of formulae (A) to (D) in accordance with the present invention have various applications as hereinafter described. Reference herein to compounds of formulae (A) to (D) should be taken to also include all individualized compounds (A1), (A2), (B1), (B2), (B3), (B4), (C1), (C2), (C3) and (D) substantially as hereinbefore described. Additionally, reference herein to compounds of formulae (A) to (D) should be taken to also include reference to salts and/or solvates thereof, and in particular should be understood to include reference to any of compounds (A) to (D) as a mesylate salt.

The inventors have found that compounds of formulae (A) to (D) as described herein, suitable for use as reference markers or reference standards, are by-products or impurities that may form during the synthesis of dabigatran etexilate and/or its salts (for example the mesylate salt (1:1)), and/or solvates (for example hydrates) substantially as hereinbefore described. Alternatively, compounds of formulae (A) to (D) can be formed further to API degradation and/or during formulation and/or during storage. In a particularly preferred embodiment, the compounds of formulae (A) to (D), especially any one of compounds of formulae (A) to (C), according to the invention are in isolated form. Most preferably, the isolated form is in substantially pure form, preferably having a purity of greater than about 90%, preferably greater than about 95%, preferably greater than about 98%, most preferably greater than about 99%, preferably as measured by HPLC.

In another aspect, the invention provides a process for determining the suitability for distribution of a batch of dabigatran etexilate and/or its salts (for example the mesylate salt (1:1)), and/or its solvates (for example hydrates), or a pharmaceutical composition comprising dabigatran etexilate and/or its salts (for example the mesylate salt (1:1)), and/or its solvates (for example hydrates) from said batch, said process comprising:

(a) producing a batch of dabigatran etexilate and/or its salts (for example the mesylate salt (1:1)), and/or its solvates (for example hydrates), or a pharmaceutical composition comprising dabigatran etexilate and/or its salts (for example the mesylate salt (1:1)), and/or its solvates (for example hydrates) from said batch;

(b) measuring the concentration of one or more of compounds of formulae (A) to (D), using respectively one or more of compounds of formulae (A) to (D) as reference marker; and (c) validating the batch for distribution only if the sample of the batch is free or substantially free of one or more of compounds of formulae (A) to (D) as hereinbefore disclosed.

In the context of the present invention, a batch of dabigatran etexilate and/or its salts (for example the mesylate salt (1:1)), and/or its solvates (for example hydrates), or a pharmaceutical composition comprising dabigatran etexilate and/or its salts (for example the mesylate salt (1:1)), and/or its solvates (for example hydrates) is to be understood as a batch of said dabigatran etexilate and/or its salts (for example the mesylate salt (1:1)), and/or its solvates (for example hydrates), or said pharmaceutical composition comprising dabigatran etexilate and/or its salts (for example the mesylate salt (1:1)), and/or its solvates (for example hydrates) is considered suitable for distribution when said batch is substantially free of any of compounds of formulae (A) to (D), i.e. it comprises not more than about 5% of any of compounds of formulae (A) to (D), preferably not more than about 3%, preferably not more than about 2%, preferably not more than about 1%, preferably not more than about 0.5%, preferably not more than about 0.1%, preferably not more than about 0.05%, preferably as measured by HPLC.

A batch of dabigatran etexilate and/or its salts (for example the mesylate salt (1:1)), and/or its solvates (for example hydrates), or a pharmaceutical composition comprising dabigatran etexilate and/or its salts (for example the mesylate salt (1:1)), and/or its solvates (for example hydrates), may be produced in step (a) by any process known in the art.

Measuring the concentration of one or more of compounds of formulae (A) to (D) in step (b), using respectively one or more of compounds of formulae (A) to (D) as reference marker, refers to determining the concentration of compounds of formulae (A) to (D) in a sample of a batch of dabigatran etexilate and/or its salts (for example the mesylate salt (1:1)), and/or its solvates (for example hydrates), or a pharmaceutical composition comprising dabigatran etexilate and/or its salts (for example the mesylate salt (1:1)), and/or its solvates (for example hydrates), produced in step (a), by means of routine quantitative analysis known for the skilled person, e.g. HPLC chromatography by reference to the concentration of a solution comprising a known amount of one or more of compounds of formulae (A) to (D).

Step (c) is the validation of the batch for distribution if the sample of the batch is free or substantially free of one or more of compounds of formulae (A) to (D). This step refers to the determination of whether the batch produced in step (a) is suitable for distribution, wherein a batch is considered "suitable for distribution" when said batch is free or substantially free of any of compounds of formulae (A) to (D), i.e. it comprises not more than about 5% of any of compounds of formulae (A) to (D), preferably not more than about 3%, preferably not more than about 2%, preferably not more than about 1%, preferably not more than about 0.5%, preferably not more than about 0.1%, preferably not more than about 0.05%, preferably as measured by HPLC. Thus, if the batch produced in step (a) is free or substantially free of any of compounds of formulae (A) to (D), said batch is validated for distribution, i.e. considered as suitable for distribution. If the batch produced in step (a) is not free or substantially free of any of compounds of formulae (A) to (D), said batch is not validated for distribution, i.e. considered as unsuitable for distribution.

In a particular embodiment of the above mentioned process for determining the suitability for distribution of a batch of dabigatran etexilate and/or its salts (for example the mesylate salt (1:1)), and/or its solvates (for example hydrates), or a pharmaceutical composition comprising dabigatran etexilate and/or its salts (for example the mesylate salt (1:1)), and/or its solvates (for example hydrates), said compound of formulae (A) to (D) is compound (A2).

In another particular embodiment of the above mentioned process for determining the suitability for distribution of a batch of dabigatran etexilate and/or its salts (for example the mesylate salt (1:1)), and/or its solvates (for example hydrates), or a pharmaceutical composition comprising dabigatran etexilate and/or its salts (for example the mesylate salt (1:1)), and/or its solvates (for example hydrates), said compound of formulae (A) to (D) is compound (B1).

In another particular embodiment of the above mentioned process for determining the suitability for distribution of a batch of dabigatran etexilate and/or its salts (for example the mesylate salt (1:1)), and/or its solvates (for example hydrates), or a pharmaceutical composition comprising dabigatran etexilate and/or its salts (for example the mesylate salt (1:1)), and/or its solvates (for example hydrates), said compound of formulae (A) to (D) is compound (B3).

In another aspect, the invention provides a method for preparing dabigatran etexilate, or a salt thereof (for example the mesylate salt (1:1)), or a solvate thereof (for example hydrates), suitable for pharmaceutical use, comprising the steps of:

(a) providing dabigatran etexilate, or a salt thereof (for example the mesylate salt (1:1)), or a solvate thereof (for example hydrates);

(b) assessing the purity of said dabigatran etexilate, or a salt thereof (for example the mesylate salt (1:1)), or a solvate thereof (for example hydrates), by using one or more of compounds of formulae (A) to (D) as reference marker to determine the concentration of said one or more compounds of formulae (A) to (D), respectively; and (c) subjecting the dabigatran etexilate, or a salt thereof (for example the mesylate salt (1:1)), or a solvate thereof (for example hydrates), to one or more purification steps; wherein step (c) is performed either before or after step (b).

In the context of the present invention, dabigatran etexilate, or a salt or solvate thereof, is considered suitable for pharmaceutical use, when it is free or substantially free of any of compounds of formulae (A) to (D), wherein "substantially free" means that said dabigatran etexilate, or salt or solvate thereof comprises not more than about 5% of any of compounds of formulae (A) to (D), preferably not more than about 3%, preferably not more than about 2%, preferably not more than about 1%, preferably not more than about 0.5%, preferably not more than about 0.1%, preferably not more than about 0.05%, preferably as measured by HPLC.

The term "reference marker", as used herein, refers to a compound that may be used in qualitative analysis to identify components of a mixture based on their position, e.g. in a HPLC chromatogram or on a Thin Layer Chromatography (TLC) plate, and/or in quantitative analysis to determine the concentration of said compound in a mixture by reference to the concentration of a solution comprising a known amount of said component. A reference marker solution will comprise one or more of compounds (A) to (D) dissolved in an appropriate solvent. The method of analysis will be apparent to a skilled addressee. Thus, assessing the purity of dabigatran etexilate, or a salt thereof (for example the mesylate salt (1:1)), or a solvate thereof (for example hydrates), by using one or more of compounds of formulae (A) to (D) as reference marker, according to step (b), means determining the concentration of said one or more compounds of formulae (A) to (D), respectively. Preferably, the concentration of said compound of formulae (A) to (D) is determined by means of conventional methods known in the art for quantifying compounds, such as HPLC.

The purification steps mentioned in step (c) refer to conventional purification techniques known by the skilled in the art, such as chromatography, digestion and crystallization, among others.

In a preferred embodiment of the above mentioned method for preparing dabigatran etexilate, or a salt thereof (for example the mesylate salt (1:1)), or a solvate thereof (for example hydrates), said compound of formulae (A) to (D) is compound (A2).

In another preferred embodiment of the above mentioned method for preparing dabigatran etexilate, or a salt thereof (for example the mesylate salt (1:1)), or a solvate thereof (for example hydrates), said compound of formulae (A) to (D) is compound (B1).

In another preferred embodiment of the above mentioned method for preparing dabigatran etexilate, or a salt thereof (for example the mesylate salt (1:1)), or a solvate thereof (for example hydrates), said compound of formulae (A) to (D) is compound (B3).

Accordingly, the invention provides the use of one or more of compounds of formulae (A) to (D) as a reference marker or reference standard to analyze the purity of dabigatran etexilate and/or its salts (for example the mesylate salt (1:1)), and/or its solvates (for example hydrates).

The term "reference standard", as used in the context of the present invention, has an equivalent meaning to "reference marker".

Specifically, the invention provides the use of one or more of compounds of formulae (A) to (D) as a reference standard to quantify the amount of one or more of compounds of formulae (A) to (D) in a sample of dabigatran etexilate and/or its salts (for example the mesylate salt (1:1)), and/or its solvates (for example hydrates). A reference standard solution will comprise a known amount of one or more of compounds of formulae (A) to (D) dissolved in an appropriate solvent.

Still further, there is provided a method of testing the purity of a sample of dabigatran etexilate and/or its salts (for example the mesylate salt (1:1)), and/or its solvates (for example hydrates), which method comprises assaying the sample for the presence of one or more of the compounds of formulae (A) to (D) according to the invention. In the method of the invention said compounds are acting as reference markers or reference standards.

A further aspect provides a chromatographic method for testing the purity of a sample of dabigatran etexilate and/or its salts (for example the mesylate salt (1:1)), and/or its solvates (for example hydrates), by determining the presence of one or more of compounds of formulae (A) to (D) in a sample comprising dabigatran etexilate and/or its salts or solvates as above, said method comprising:

(a) dissolving a sample of dabigatran etexilate and/or its salts (for example the mesylate salt (1:1)), and/or its solvates (for example hydrates), in a solvent to produce a sample solution;

(b) dissolving a sample of one or more of compounds of formulae (A) to (D) in a solvent to produce a reference marker solution;

(c) subjecting the sample solution and the reference marker solution to a chromatographic technique; and (d) determining in the sample of dabigatran etexilate and/or its salts the presence of one or more of compounds of formulae (A) to (D) in the sample by reference to the presence of one or more of compounds of formulae (A) to (D) present in the reference marker solution.

The determination of the presence of one or more compounds of formula (A) to (D) in the sample of dabigatran etexilate and/or its salts is effected by comparing the retention (retention time in HPLC, retention factor in TLC, . . . ) of the different components of the sample of dabigatran etexilate and/or its salts separated by the chromatographic technique with the retention of the compounds of formulae (A) to (D) under the same chromatographic conditions (i.e. stationary phase, mobile phase, temperature, pressure, . . . ).

Preferably, the chromatographic method is a liquid chromatographic method such as a HPLC method.

In the context of the present invention, "comparing the retention" is to be understood as determining whether two retention values are substantially the same, for example the first value being the retention of one of the different components of the sample of dabigatran etexilate and/or its salts separated by the chromatographic technique and the second value being the retention of one of compounds of formulae (A) to (D) under the same chromatographic conditions, and wherein "substantially the same" means that the retention values differ in less than a 10%, preferably less than a 5%, even more preferably less than a 1%, still more preferably less than a 0.5%, the most preferred less than a 0.1%.

In another embodiment, the invention provides a method for analyzing the amount of one or more of compounds of formulae (A) to (D) present in a sample of dabigatran etexilate and/or its salts (for example the mesylate salt (1:1)), and/or its solvates (for example hydrates), using analytical HPLC, said method comprising:

(a) measuring by HPLC the area under the peak corresponding to one or more of compounds of formulae (A) to (D) in a sample of dabigatran etexilate and/or its salts (for example the mesylate salt (1:1)), and/or its solvates (for example hydrates), having an unknown amount of one or more of compounds of formulae (A) to (D);

(b) measuring by HPLC the area under a peak corresponding to one or more of compounds of formulae (A) to (D) in a reference standard solution having a known amount of said one or more compounds of formulae (A) to (D); and (c) determining the amount of said one or more compounds of formulae (A) to (D) in the sample of dabigatran etexilate and/or its salts (for example the mesylate salt (1:1)), and/or its solvates (for example hydrates), by comparing the area calculated in step (a) with the area calculated in step (b).

In still another embodiment, the invention provides a process for analyzing the purity of a sample of dabigatran etexilate and/or its salts (for example the mesylate salt (1:1)), and/or its solvates (for example hydrates), comprising monitoring the amount of one or more compounds of formulae (A) to (D) in said sample typically by employing HPLC substantially as described above.

A sample of dabigatran to be tested by a method according to the present invention comprises, or is derived from, one of the following:

(a) dabigatran etexilate API; or (b) a pharmaceutical composition comprising dabigatran etexilate; or (c) a dabigatran etexilate salt (for example the mesylate salt (1:1)), and/or a solvate (for example hydrate); or (d) a pharmaceutical composition comprising a dabigatran etexilate salt (for example the mesylate salt (1:1)), and/or a solvate (such as a hydrate).

Preferably, the dabigatran tested by a method of testing the purity of dabigatran according to the present invention is suitable for use in a pharmaceutical composition.

A further aspect of the present invention provides dabigatran etexilate and/or its salts (for example the mesylate salt (1:1)), and/or its solvates (for example hydrates), which has been subjected to a purification method whereby the control of the purity is effected with the help of a method of testing the purity of the dabigatran according to the present invention. According to the present invention, there is thus provided dabigatran etexilate and/or its salts (for example the mesylate salt (1:1)), and/or its solvates (for example hydrates), which includes pharmaceutically acceptable amounts of one or more of compounds of formulae (A) to (D). In a particular embodiment, the present invention provides dabigatran etexilate and/or its salts (for example the mesylate salt (1:1)), and/or its solvates (for example hydrates), that can be described as substantially free of one or more of compounds of formulae (A) to (D).

Dabigatran etexilate is "substantially free" of a compound, if it comprises not more than about 5% of that compound, preferably not more than about 3%, preferably not more than about 2%, preferably not more than about 1%, preferably not more than about 0.5%, preferably not more than about 0.1%, preferably not more than about 0.05%, preferably as measured by HPLC. Such dabigatran etexilate is typically as prepared by a process according to the present invention as described herein.

A still further aspect of the present invention provides a pharmaceutical composition comprising dabigatran etexilate according to the present invention.

Still further, there is provided a method for the characterization of the compounds of formulae (A) to (D) using a HPLC method for the analysis of said one or more compounds of formulae (A) to (D) in dabigatran etexilate and/or its salts (for example the mesylate salt (1:1)), and/or its solvates (for example hydrates).

The present invention has particular applicability in monitoring potential degradation and ensuring required potency of dabigatran etexilate mesylate, in that dabigatran etexilate mesylate is susceptible to potential product breakdown from moisture resulting in potential loss of potency. For this reason, pharmaceutical compositions comprising dabigatran etexilate mesylate should generally only be dispensed and stored in its originally provided packaging, such as an original bottle or blister package. Re-packaging should be avoided in view of the above.

In particular in accordance with the present invention, the use of a compound of formula (B), especially compound (B3), is particularly beneficial for use as a reference marker or reference standard for monitoring the purity and as such potential degradation profile of dabigatran etexilate mesylate substantially as hereinbefore described. In this way, the purity profile and associated potency of dabigatran etexilate mesylate as present in a pharmaceutical composition can be suitably monitored, and the invention also further provides a method of monitoring such purity and as such degradation profile of dabigatran etexilate mesylate over time. Based on such analysis, the present invention further provides a pharmaceutical composition comprising dabigatran etexilate mesylate, which on storage for at least three months at 40° C. and 75% relative humidity, typically in a double polyethylene bag, includes less than about 10% of a compound of formula (B), especially compound (B3), relative to dabigatran etexilate, preferably less than about 9%, preferably less than about 8%, and even more preferably in an amount of about 7.55 to 7.70%. The inventors have found that it is particularly beneficial to monitor a compound of formula (B), especially compound (B3), so as to obtain a meaningful indication as to the extent of dabigatran etexilate mesylate degradation potentially occurring in a pharmaceutical composition comprising dabigatran etexilate mesylate, and in particular to obtain a meaningful indication as to the extent of potential hydrolysis that might occur in view of the presence of moisture, such as atmospheric moisture, in a storage environment. Furthermore, the inventors consider the formation of a compound of formula (B), especially compound (B3), as a main hydrolysis product from dabigatran etexilate mesylate on storage to be particularly surprising in view of the different main hydrolysis product that is obtained from dabigatran etexilate mesylate in vivo. More specifically, in vivo hydrolysis of dabigatran etexilate mesylate mainly results in the formation of a compound of formula (D1), namely dabigatran, and the formation of a compound of formula (B), especially compound (B3), has not previously been reported. On this basis, the formation of a compound of formula (B), especially compound (B3), as a main hydrolysis product from dabigatran etexilate mesylate on storage could not have been predicted based on the disclosure of the prior art.

The term "about" when used in the present invention preceding a number and referring to it, is meant to designate any value which lies within the range defined by the number±10% of its value, preferably a range defined by the number±5%, more preferably range defined by the number±2%, still more preferably a range defined by the number±1%. For example "about 10" should be construed as meaning within the range of 9 to 11, preferably within the range of 9.5 to 10.5, more preferably within the range of 9.8 to 10.2, and still more preferably within the range of 9.9 to 10.1.

There is still further provided by the present invention, a process of preparing dabigatran etexilate and/or its salts (for example the mesylate salt (1:1)), and/or its solvates (for example hydrates), wherein one or more of compounds of formulae (A) to (D) forms in said process. Preferably the process further comprises testing the purity of dabigatran etexilate and/or its salts (for example the mesylate salt (1:1)), and/or its solvates (for example hydrates) substantially as hereinbefore described and purifying the product by any conventional purification method until the purified product is substantially free of one or more of compounds of formulae (A) to (D).

There is still further provided by the present invention a process of preparing dabigatran etexilate mesylate, which process comprises the following synthetic steps:

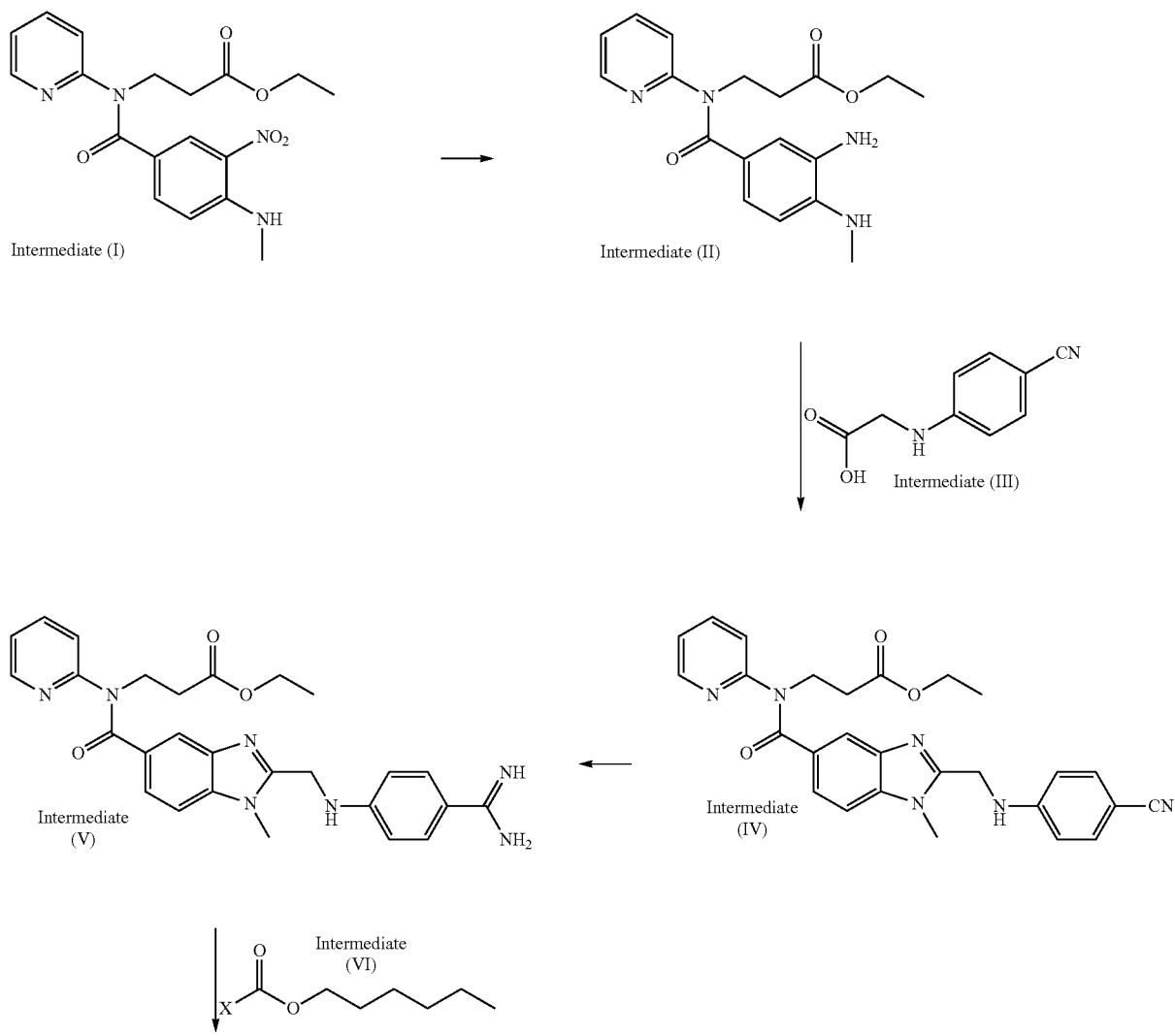

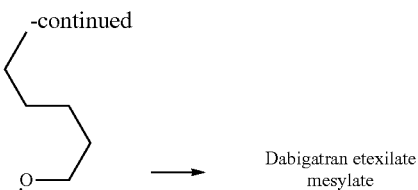

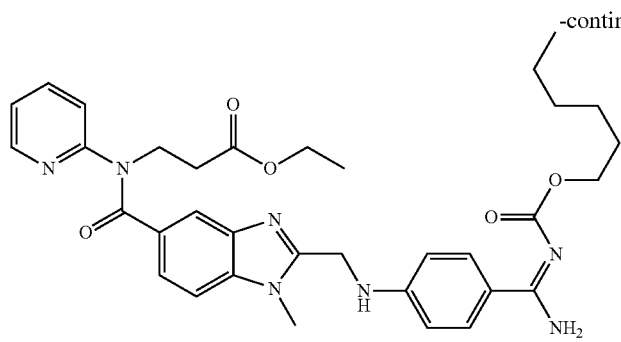

Dabigatran etexilate

→ Dabigatran etexilate mesylate wherein X is a leaving group, such as chloro.

Further preferred aspects of the above process according to the present invention can be as follows.

Intermediate (I) above is preferably isolated as a hydrochloride salt in a process according to the present invention, whereas preferably intermediate (V) above is isolated as the free base. Typically, intermediate (I) is prepared, preferably as a hydrochloride salt, by the following intermediate steps.

The following examples further illustrate the invention but, of course, should not be construed as in any way limiting its scope.

EXAMPLES

General Experimental Conditions

HPLC Method 1

The chromatographic separation was carried out in a Kromasil 100-5C18, 5 μm, 4.6×250 mm column at 25° C.

The mobile phase was prepared by filtering and degassing an acetonitrile/buffer solution (45:55) v/v mixture. The buffer solution was obtained by preparing a 50 mM formic acid solution in water and adjusting the pH to 3.8 with ammonium hydroxide.

The chromatograph was equipped with a 254 nm detector and the flow rate was 1.0 mL per minute. 20 μL of the test samples were injected. The samples were prepared by dissolving the appropriate amount of sample in mobile phase, to obtain a concentration of about 1.0 mg/mL. The chromatogram was run for at least 30 min. The approximate retention time for dabigatran etexilate was found to be 9.2 min.

HPLC Method 2:

The chromatographic separation was carried out in a Kromasil 100-5C18, 5 μm, 4.6×250 mm column at 25° C.

The mobile phase was prepared by filtering and degassing an acetonitrile/buffer solution (35:65) v/v mixture. The buffer solution was obtained by preparing a 50 mM formic acid solution in water and adjusting the pH to 3.8 with ammonium hydroxide.

The chromatograph was equipped with a 254 nm detector and the flow rate was 1.0 mL per minute. 20 μL of the test samples were injected. The samples were prepared by dissolving the appropriate amount of sample in mobile phase, to obtain a concentration of about 1.0 mg/mL. The chromatogram was run for at least 40 min.

HPLC Method 3:

The chromatographic separation was carried out in a Kromasil 100-5C18, 5 μm, 4.6×250 mm column at 25° C.

The mobile phase was prepared by filtering and degassing an acetonitrile/methanol/buffer solution (1:1:3) v/v mixture. The buffer solution was obtained by preparing a 50 mM formic acid solution in water and adjusting the pH to 3.8 with ammonium hydroxide.

The chromatograph was equipped with a 254 nm detector and the flow rate was 1.0 mL per minute. 20 μL of the test samples were injected. The samples were prepared by dissolving the appropriate amount of sample in mobile phase, to obtain a concentration of about 1.0 mg/mL. The chromatogram was run for at least 30 min.

Example 1

Synthesis of Dabigatran Etexilate Mesylate

The overall synthetic scheme, and associated reagents, is as follows.

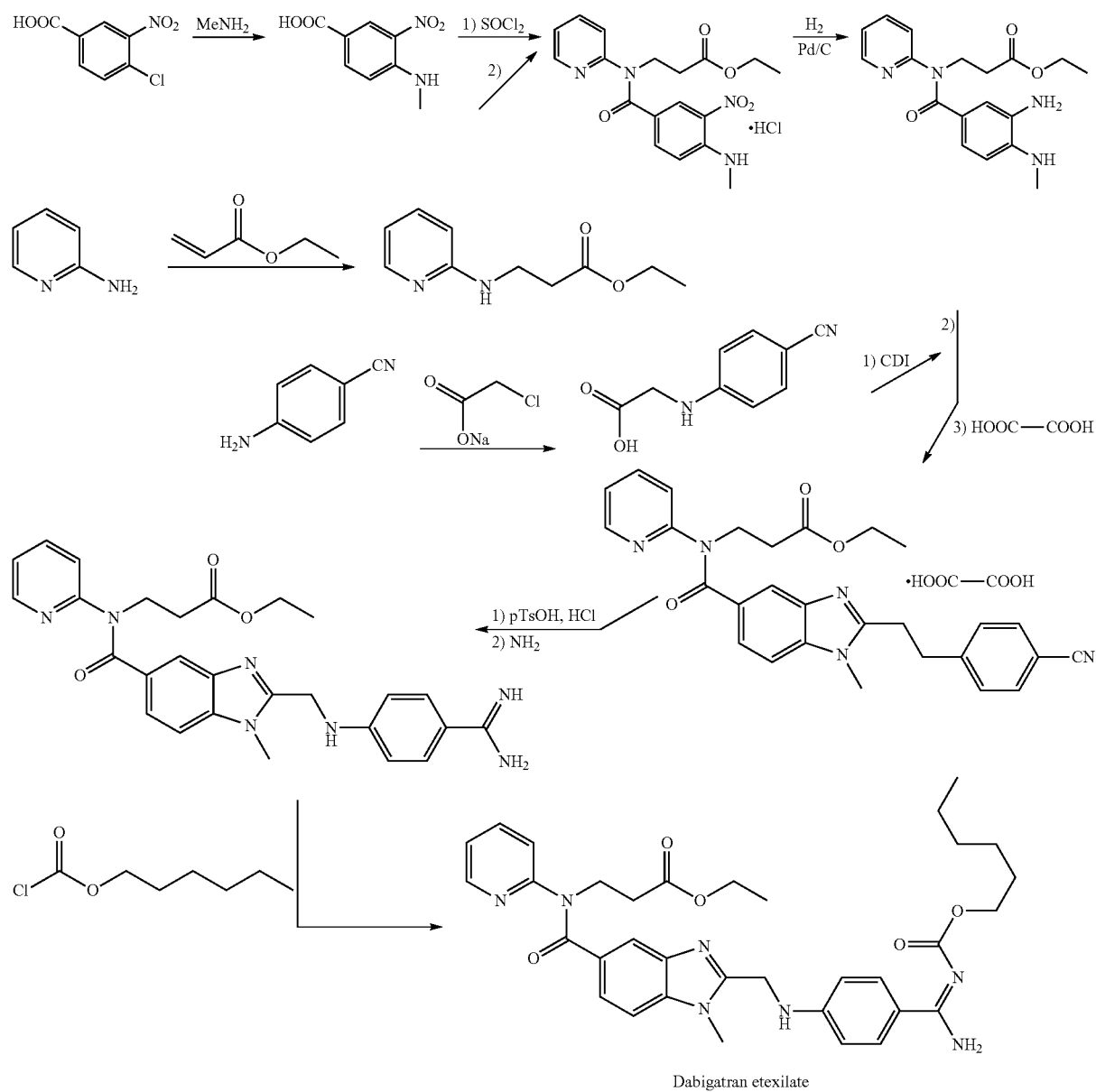

a) 4-(Methylamino)-3-nitrobenzoic Acid

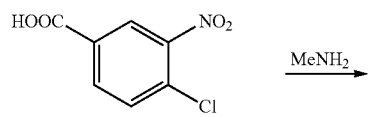

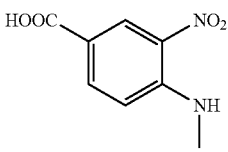

300 g (1.49 mol) of 4-chloro-3-nitrobenzoic acid were suspended in 769 g of a 25-30% aqueous solution of methylamine. After heating to reflux temperature, a clear solution was obtained. The solution was kept at reflux temperature for 2 hours and total consumption of 4-chloro-3-nitrobenzoic acid was checked by TLC. The solution was cooled to room temperature, and pH was adjusted to about 1 by addition of 2M aqueous sulphuric acid. Precipitation of a yellow solid was observed, which was isolated by filtration. The filtered cake was washed with water and subsequently with methanol to obtain 331 g of wet 4-(methylamino)-3-nitrobenzoic acid as a yellow powder. Purity (HPLC, method 2): 99.1%.

b) Ethyl 3-(2-pyridylamino)propanoate

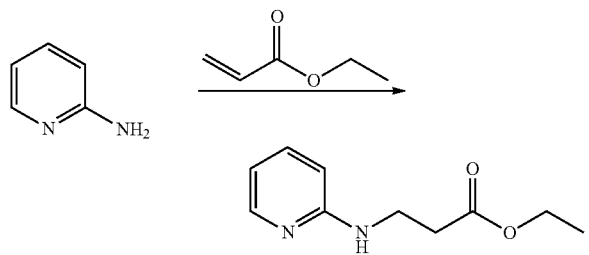

75.2 g (0.80 mol) of 2-aminopyridine and 88.0 g (0.88 mol) of ethyl acrylate were dissolved in 20 mL of acetic acid. The mixture was heated to 80° C. and stirred for 24 hours at the same temperature. Solvent was removed under vacuum, and the title compound was isolated by vacuum distillation (b.p. 160-172° C., 10-15 mmHg) to obtain 77.0 g of ethyl 3-(2-pyridylamino)propionate as a white solid. Yield: 49.6%.

c) Ethyl 3-{[{1-(methylamino)-2-nitrophen-4-yl}carbonyl](pyridyn-2-yl)amino}propanoate Hydrochloride

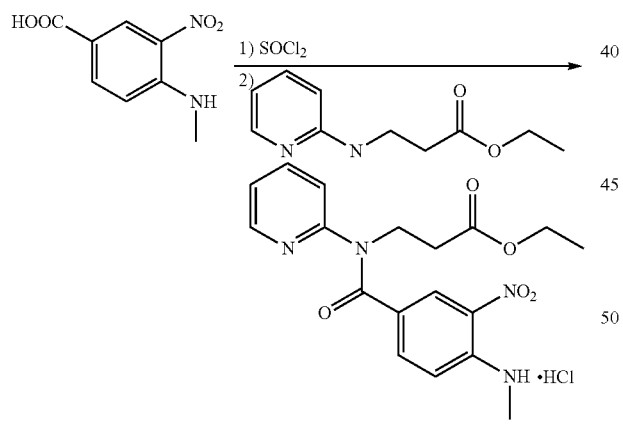

50 g (0.25 mol) of 4-(methylamino)-3-nitrobenzoic acid as obtained in step (a) were suspended in a mixture of 459.2 g of thionyl chloride and 3 mL of N,N-dimethylformamide. The mixture was stirred at reflux temperature for 45 minutes. Excess thionyl chloride was removed by vacuum distillation. The residue was dissolved in 300 mL of toluene, which was subsequently removed by vacuum distillation to remove completely any residual thionyl chloride. The brownish crystalline residue obtained was dissolved in 280 mL of tetrahydrofuran at 60° C. At this point, 35.1 g of triethylamine were added to the solution. Then, a solution of 45 g (0.23 mol) of ethyl 3-(2-pyridylamino)propanoate as obtained in step (b) in 95 mL of tetrahydrofuran was added dropwise over the reaction mixture, keeping the temperature at about 30° C. The resulting mixture was stirred overnight at room temperature. Solvent was removed by vacuum distillation, and the residue was dissolved in 1 L of dichloromethane. The resulting solution was washed with 500 mL of water, 500 mL of 2M hydrochloric acid, 500 mL of saturated sodium bicarbonate and 500 mL of water. The organic phase was dried with anhydrous sodium sulfate and concentrated under vacuum. The residue was dissolved with 600 mL of ethyl acetate, and dry hydrogen chloride was bubbled into the solution until precipitation was completed. The solid was isolated by filtration and dried to obtain 63 g of the title compound, which was recrystallized in a mixture of 450 mL of ethanol and 50 mL of acetonitrile at reflux temperature. After cooling to 10° C., solid was isolated by filtration and dried to yield 44.7 g of ethyl 3-{[{1-(methylamino)-2-nitrophen-4-yl}carbonyl](pyridyn-2-yl)amino}propanoate hydrochloride as a yellow solid. Yield: 47.2%. Purity (HPLC, method 1): 97.6%.

d) Ethyl 3-{[{2-amino-1-(methylamino)phen-4-yl}carbonyl](pyridyn-2-yl)amino}propanoate (Compound II)

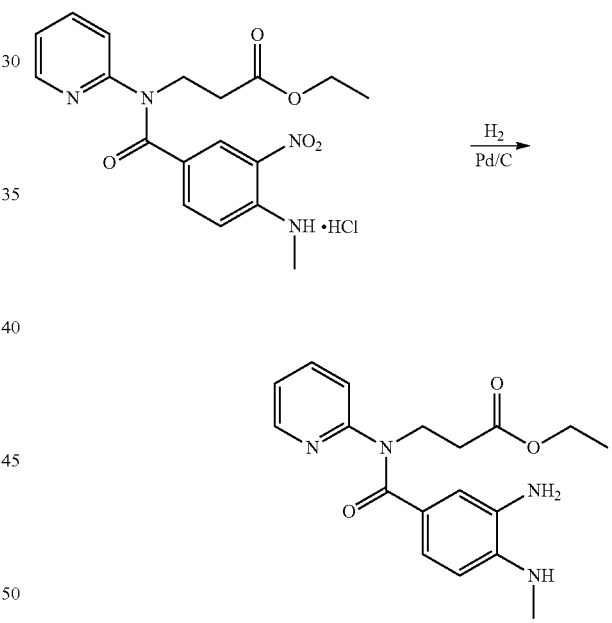

82.2 g (0.20 mol) of ethyl 3-{[{1-(methylamino)-2-nitrophen-4-yl}carbonyl](pyridyn-2-yl)amino}propanoate hydrochloride as obtained in step (c) were suspended in 1.1 L of isopropanol, in the presence of 126.7 g of ammonium formate and 17.5 g of a 5% Pd/C catalyst (55% water content). The reaction mixture was stirred at reflux temperature for 2.5 hours. After cooling to room temperature, the catalyst was removed by filtration, the filtrate was concentrated under vacuum, and the residue was dissolved in 1.5 L of ethyl acetate. The resulting solution was washed with 800 mL of saturated sodium bicarbonate and with 800 mL of water. The organic phase was dried with anhydrous sodium sulfate and was concentrated under vacuum to yield 44 g of ethyl 3-{[{2- amino-1-(methylamino)phen-4-yl}carbonyl](pyridyn-2-yl)amino}propanoate as a dark oil. Yield: 63.9%. Purity (HPLC, method 2): 90.8%.

e) 2-(4-Cyanophenylamino)acetic Acid (Compound III)

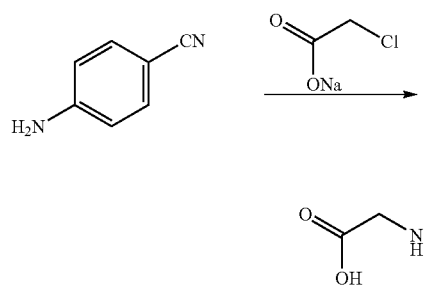

54.0 g (0.46 mol) of 4-aminobenzonitrile and 106.5 g (0.92 mol) of sodium chloroacetate were suspended in 750 mL of water, and the resulting mixture was stirred at reflux temperature for 4 hours. After cooling to room temperature, pH was adjusted to 8-9 with sodium bicarbonate. The resulting solution was washed with 2×200 mL of ethyl acetate, and 5M hydrochloric acid was added to the aqueous phase until pH=3. The precipitated solid was isolated by filtration, washed with 100 mL of water and dried to yield 57.1 g of 2-(4-cyanophenylamino)acetic acid as an off-white solid. Yield: 70.9%. Purity (HPLC, method 3): 88.4%.

f) Ethyl 3-{[(2-{[(4-cyanophenyl)amino]methyl}-1-methyl-1H-benzimidazol-5-yl)carbonyl](pyridin-2-yl)amino}propanoate Oxalate (Salt of Compound IV)

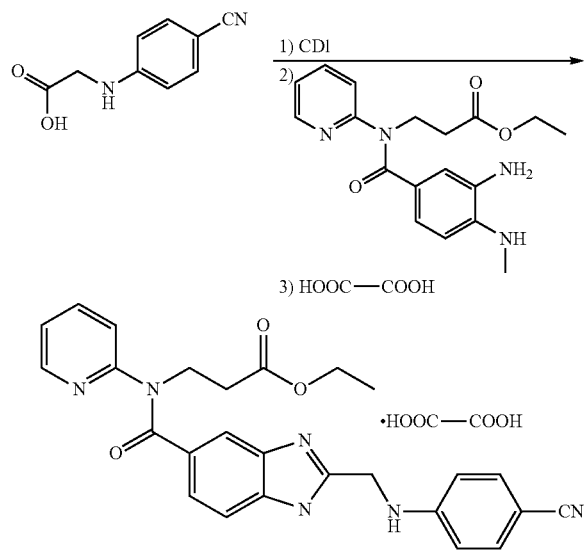

25.7 g (0.15 mol) of 2-(4-cyanophenylamino)acetic acid as obtained in step (e) and 22.8 g (0.14 mol) of 1,1'-carbonyldiimidazole were suspended in 720 mL of tetrahydrofuran. The mixture was stirred at reflux temperature for 1 hour. Then, a solution of 44.0 g (0.13 mol) of ethyl 3-{[{2-amino-1-(methylamino)phen-4-yl}carbonyl](pyridyn-2-yl)amino}propanoate as obtained in step (d) in 180 mL of tetrahydrofuran was added dropwise over the reaction mixture. The resulting mixture was stirred overnight at reflux temperature, and the solvent was removed by distillation under vacuum. The resulting residue was dissolved in 486 mL of acetic acid and heated to reflux temperature for 1 hour. After cooling to room temperature, solvent was removed by distillation under vacuum. The resulting residue was dissolved in 450 mL of ethyl acetate, and the solution was washed with 450 mL of water. The organic phase was dried with anhydrous sodium sulfate and heated to 50-60° C. At this temperature, 15.1 g (0.17 mol) of oxalic acid were added, and the resulting mixture was stirred for 1 hour at 50-60° C. After cooling to room temperature, the precipitated solid was filtered and dried under vacuum, to yield 47.7 g of ethyl 3-{[(2-{[(4-cyanophenyl)amino]methyl}-1-methyl-1H-benzimidazol-5-yl)carbonyl](pyridin-2-yl)amino}propanoate oxalate as a brownish solid. Yield: 64.8%. Purity (HPLC, method 1): 87.9% g) Ethyl 3-{[(2-{[(4-{carbamimidoyl}phenyl)amino]methyl}-1-methyl-1H-benzimidazol-5-yl)carbonyl](pyridin-2-yl)amino}propanoate (Compound V)

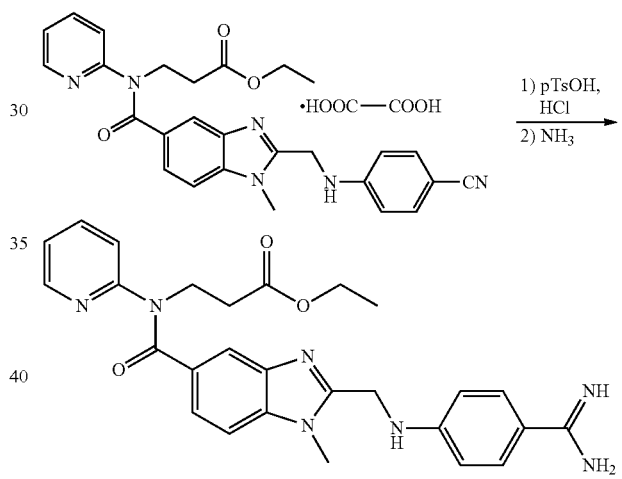

47.7 g (83 mmol) of ethyl 3-{[(2-{[(4-cyanophenyl)amino]methyl}-1-methyl-1H-benzimidazol-5-yl)carbonyl](pyridin-2-yl)amino}propanoate oxalate as obtained in step (f) and 21.8 g of p-toluenesulfonic acid were suspended in 142 g of a 10M hydrogen chloride solution in ethanol. The mixture was stirred at room temperature for 24 hours. At this point, 400 mL of ethanol were added and the resulting mixture was cooled to 0° C. Ammonia gas was bubbled at this temperature until formation of precipitate was completed. The mixture was stirred at 10° C. for 2 hours, and then was stirred at room temperature overnight. Solvent was removed by distillation under vacuum. The residue was dissolved in a mixture of 400 mL of ethanol, 400 mL of water and 2.3 g of sodium hydroxide at 55° C., and was stirred at this temperature for 45 minutes. After cooling to 10° C., the mixture was stirred at this temperature for 1 hour. The solid was removed by filtration and discarded. The mother liquors were concentrated under vacuum to remove ethanol. The precipitated solid was isolated by filtration, washed with 200 mL of water and with 2×100 mL of acetone, to yield 34.7 g of ethyl 3-{[(2-{[(4-{carbamimidoyl}phenyl)amino]methyl}-1-methyl-1H-benzimidazol-5-yl)carbonyl](pyridin-2-yl)amino}propanoate as an off-white solid. Yield: 83.4%. Purity (HPLC, method 3): 83%.

h) Dabigatran Etexilate

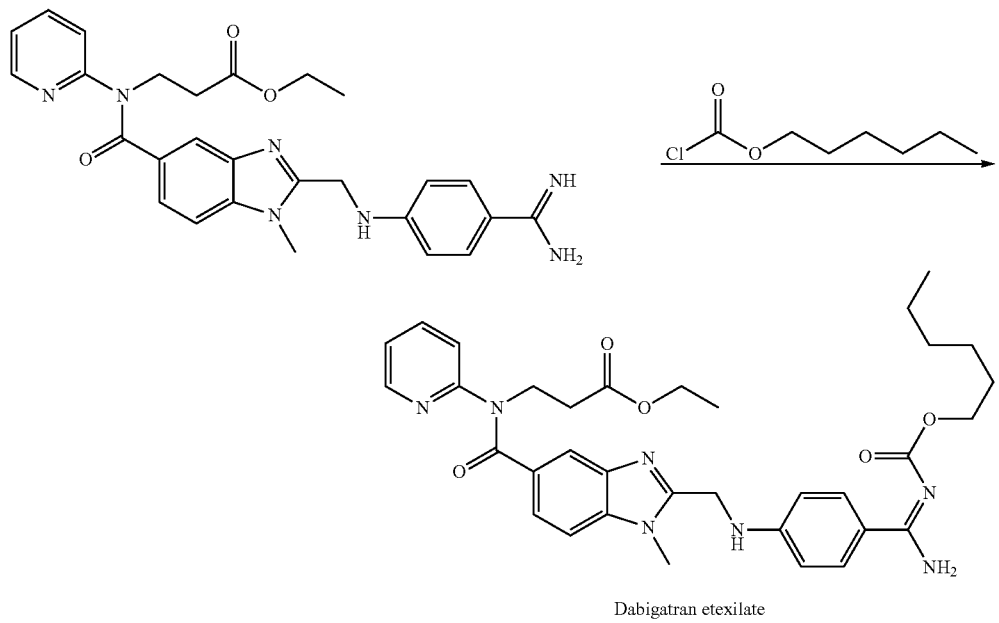

Dabigatran etexilate 33.7 g (67 mmol) of ethyl 3-{[(2-{[(4-{carbamimidoyl}phenyl)amino]methyl}-1-methyl-1H-benzimidazol-5-yl)carbonyl](pyridin-2-yl)amino}propanoate as obtained in step (g) and 24.7 g of potassium carbonate were suspended in a mixture of 280 mL of water and 1.4 L of tetrahydrofuran. After stirring at room temperature for 15 minutes, 9.2 g (56 mmol) of hexyl chloroformate were added dropwise. The resulting mixture was stirred at room temperature for 1 hour. The organic phase was extracted, washed with 400 mL of brine and dried with anhydrous sodium sulfate. The solvent was removed under vacuum, and the resulting solid was purified by column chromatography eluting with ethyl acetate, to yield 24.9 g of dabigatran etexilate as an off-white solid. Yield: 71.0%. Purity (HPLC, method 1): 96.3%.

i) Dabigatran Etexilate Mesylate 18.7 g (30 mmol) of dabigatran etexilate as obtained in step (h) were suspended in 103 g of acetone. The mixture was heated to 45° C. After cooling to 36° C., a solution of 2.83 g of methanesulfonic acid in 11.6 g of acetone at 0° C. was added dropwise over the reaction mixture. The reaction was stirred at 23-33° C. for 90 minutes and at 17-23° C. for 60 minutes. The resulting solid was isolated by filtration, washed with 97 mL of acetone and dried at 50° C. under vacuum, to yield 18.7 g of dabigatran etexilate mesylate as a pale yellow solid. Yield: 86.7%. Purity (HPLC, method 1): 98.8%.

Example 2

Synthesis of Dabigatran Etexilate Mesylate a) 4-(Methylamino)-3-nitrobenzoic Acid 300 g (1.49 mol) of 4-chloro-3-nitrobenzoic acid were suspended in 836 mL of a 25-30% aqueous solution of methylamine. After heating to reflux temperature, an orange solution was obtained. The solution was kept at reflux temperature for 4 hours. The solution was cooled to room temperature, and pH was adjusted to about 2 by addition of 2M aqueous sulphuric acid. Precipitation of an orange solid was observed, which was isolated by filtration. The filtered cake was washed with 1.5 L of water and subsequently with 750 mL of ethanol. The solid was suspended in 1.6 L of ethanol and stirred at reflux temperature for 30 minutes. After cooling to room temperature, the solid was filtered and dried at 60° C. under vacuum to obtain 285 g of 4-(methylamino)-3-nitrobenzoic acid as an orange powder. Yield: 97.5%. Purity (HPLC, method 2): 97.7%.

b) Ethyl 3-(2-pyridylamino)propanoate 200 g (2.12 mol) of 2-aminopyridine and 346 mL (3.19 mol) of ethyl acrylate were dissolved in 53 mL of acetic acid. The mixture was heated to 88° C. and stirred overnight at this temperature. Solvent was removed under vacuum, and the title compound was purified by column chromatography, eluting with ethyl acetate, to obtain 360 g of ethyl 3-(2-pyridylamino)propionate as a white solid. Yield: 86.7%.

c) Ethyl 3-{[{1-(methylamino)-2-nitrophen-4-yl}carbonyl](pyridyn-2-yl)amino}propanoate Hydrochloride 106 g (0.54 mol) of 4-(methylamino)-3-nitrobenzoic acid as obtained in step (a) were suspended in a mixture of 911 mL of thionyl chloride and 10 mL of N,N-dimethylformamide. The mixture was stirred at reflux temperature for 3 hours. Excess thionyl chloride was removed by vacuum distillation. The residue was dissolved in 200 mL of toluene, which was subsequently removed by vacuum distillation to remove any residual thionyl chloride. This step of dissolving in 200 mL of toluene and removing the solvent by vacuum distillation was repeated. The residue was dissolved in 500 mL of tetrahydrofuran at 5° C. At this point, 101 mL of triethylamine were added to the solution. Then, a solution of 100 g (0.51 mol) of ethyl 3-(2-pyridylamino)propanoate as obtained in step (b) in 180 mL of tetrahydrofuran was added dropwise over the reaction mixture. The resulting mixture was stirred overnight at room temperature. The solid was filtered and washed with 2×200 mL of tetrahydrofuran. The solid was discarded and the mother liquors were concentrated under vacuum. The residue was dissolved in 600 mL of dichloromethane. The resulting solution was washed with 500 mL of water, 500 mL of 2M hydrochloric acid and 500 mL of water. The organic phase was dried with anhydrous sodium sulfate and concentrated under vacuum. The residue was dissolved with 600 mL of ethyl acetate, and dry hydrogen chloride was bubbled into the solution until precipitation was completed. The suspension was stirred at room temperature for 1 hour. The solid was isolated by filtration and dried to obtain 220 g of the title compound, which was stirred with 300 mL of ethanol at reflux temperature. The suspension was cooled to room temperature and stirred overnight. The solid was isolated by filtration and dried at 50° C. under vacuum for 5 hours to yield 122 g of ethyl 3-{[{1-(methylamino)-2-nitrophen-4-yl}carbonyl](pyridyn-2-yl)amino}propanoate hydrochloride as an orange solid. Yield: 58.0%. Purity (HPLC, method 1): 95.7%.

d) Ethyl 3-{[{2-amino-1-(methylamino)phen-4-yl}carbonyl](pyridyn-2-yl)amino}propanoate (Compound II)

120 g (0.29 mol) of ethyl 3-{[{1-(methylamino)-2-nitrophen-4-yl}carbonyl](pyridyn-2-yl)amino}propanoate hydrochloride as obtained in step (c) were suspended in 1.5 L of ethanol, in the presence of 92.6 g of ammonium formate and 24 g of Pd over charcoal. The reaction mixture was stirred at reflux temperature for 3 hours. After cooling to room temperature, the catalyst was removed by filtration, the filtrate was concentrated under vacuum, and the residue was dissolved in 650 mL of ethyl acetate. The resulting solution was washed with 500 mL of saturated sodium bicarbonate and with 500 mL of water. The organic phase was dried with anhydrous sodium sulfate and was concentrated under vacuum. The residue was dissolved in 200 mL of ethanol and the resulting solution was cooled at 0° C. overnight. The precipitated solid was filtered, washed with 2×30 mL of ethanol and dried at 50° C. under vacuum for 3 hours, to yield 37.7 g of ethyl 3-{[{2-amino-1-(methylamino)phen-4-yl}carbonyl](pyridyn-2-yl)amino}propanoate as a brownish solid. Yield: 37.5%. Purity (HPLC, method 2): 99.2%.

e) 2-(4-Cyanophenylamino)acetic Acid (Compound III)

77.4 g (0.66 mol) of 4-aminobenzonitrile and 150 g (1.31 mol) of sodium chloroacetate were suspended in 1.1 L of water, and the resulting mixture was stirred at reflux temperature for 6.5 hours. After cooling to 0° C., the resulting suspension was stirred at this temperature overnight. The solid was filtered and washed with 200 mL of water. The resulting solid was suspended in 200 mL of ethyl acetate and stirred at room temperature for 1 hour. The solid was filtered, washed with 400 mL of ethyl acetate and dried at 60° C. under vacuum for 5 hours to yield 84.5 g of 2-(4-cyanophenylamino)acetic acid as an off-white solid. Yield: 73.2%. Purity (HPLC, method 3): 98.4%.

f) Ethyl 3-{[(2-{[(4-cyanophenyl)amino]methyl}-1-methyl-1H-benzimidazol-5-yl)carbonyl](pyridin-2-yl)amino}propanoate Oxalate (Salt of Compound IV)

14.1 g (80 mmol) of 2-(4-cyanophenylamino)acetic acid as obtained in step (e) and 14.0 g (86 mmol) of 1,1'-carbonyldiimidazole were suspended in 600 mL of tetrahydrofuran. The mixture was stirred at reflux temperature for 1 hour. Then, a solution of 24.4 g (71 mmol) of ethyl 3-{[{2-amino-1-(methylamino)phen-4-yl}carbonyl](pyridyn-2-yl)amino}propanoate as obtained in step (d) in 100 mL of tetrahydrofuran was added dropwise over the reaction mixture. The resulting mixture was stirred at reflux temperature for 10 hours, and the solvent was removed by distillation under vacuum. The resulting residue was dissolved in 300 mL of acetic acid and heated to reflux temperature for 1 hour. After cooling to room temperature, solvent was removed by distillation under vacuum. The resulting residue was dissolved in 400 mL of dichloromethane, and the solution was washed with 2×400 mL of water. The organic phase was dried with anhydrous sodium sulfate and the solvent was removed under vacuum. The residue was dissolved in 350 mL of ethyl acetate at 40° C. At this temperature, 12.6 g (0.14 mol) of oxalic acid were added, and the resulting mixture was stirred for 30 minutes at 40° C. After cooling to room temperature, the precipitated solid was filtered and dried at 60° C. under vacuum, to yield 35.8 g of ethyl 3-{[(2-{[(4-cyanophenyl)amino]methyl}-1-methyl-1H-benzimidazol-5-yl)carbonyl](pyridin-2-yl)amino}propanoate oxalate as a brownish solid. Yield: 87.7%. Purity (HPLC, method 1): 92.6%

111.2 g of ethyl 3-{[(2-{[(4-cyanophenyl)amino]methyl}-1-methyl-1H-benzimidazol-5-yl)carbonyl](pyridin-2-yl)amino}propanoate oxalate obtained from some batches obtained by the same process were combined at this point and suspended in 2 L of ethanol at reflux temperature for 1 hour. After cooling to room temperature, the solid was filtered, washed with 100 mL of ethanol and dried at 60° C. under vacuum to yield 92.1 g of ethyl 3-{[(2-{[(4-cyanophenyl)amino]methyl}-1-methyl-1H-benzimidazol-5-yl)carbonyl](pyridin-2-yl)amino}propanoate oxalate as an off-white solid. Yield: 82.8%.

g) Ethyl 3-{[(2-{[(4-{carbamimidoyl}phenyl)amino]methyl}-1-methyl-1H-benzimidazol-5-yl)carbonyl](pyridin-2-yl)amino}propanoate (Compound V)

92.1 g (0.16 mol) of ethyl 3-{[(2-{[(4-cyanophenyl)amino]methyl}-1-methyl-1H-benzimidazol-5-yl)carbonyl](pyridin-2-yl)amino}propanoate oxalate as obtained in step (f) were suspended in 195 mL of a 10M hydrogen chloride solution in ethanol. The mixture was stirred at room temperature for 48 hours. At this point, 500 mL of ethanol were added and the resulting mixture was cooled below 10° C. Ammonia gas was bubbled at this temperature until formation of precipitate was completed. The mixture was stirred at room temperature overnight. Solvent was removed by distillation under vacuum. The residue was dissolved in a mixture of 470 mL of ethanol and 950 mL of water at 50° C. 14.4 g of sodium hydroxide were added at this point, and the resulting solution was stirred at this temperature for 45 minutes. After cooling to room temperature, the solid was removed by filtration and discarded. The mother liquors were concentrated under vacuum to remove ethanol. The precipitated solid was isolated by filtration, washed with 1 L of water and with 500 mL of acetone, and dried at 50° C. under vacuum for 4 hours to yield 61.2 g of crude ethyl 3-{[(2-{[(4-{carbamimidoyl}phenyl)amino]methyl}-1-methyl-1H-benzimidazol-5-yl)carbonyl](pyridin-2-yl)amino}propanoate as an off-white solid. Yield: 70.0%. Purity (HPLC, method 3): 82.1%.

50.0 g of crude product were dissolved in 800 mL of methanol at 45° C. Then, 800 mL of ethyl acetate were added dropwise, and the resulting solution was cooled to 15° C. The precipitated solid was isolated by filtration and dissolved again in 750 mL of methanol at 45° C. Then, 750 mL of ethyl acetate were added dropwise, and the resulting solution was cooled to 15° C. and stirred overnight at this temperature. The precipitated solid was isolated by filtration and dried at 50° C. under vacuum for 5 hours, to yield 28.0 g of ethyl 3-{[(2-{[(4-{carbamimidoyl}phenyl)amino]methyl}-1-methyl-1H-benzimidazol-5-yl)carbonyl](pyridin-2-yl)amino}propanoate. Yield: 42.7%. Purity (HPLC, method 3): 94.8%. Content of compound (A2) (HPLC, method 1): 1.4%.

h) Dabigatran Etexilate Mesylate 5.0 g (10 mmol) of ethyl 3-{[(2-{[(4-{carbamimidoyl}phenyl)amino]methyl}-1-methyl-1H-benzimidazol-5-yl)carbonyl](pyridin-2-yl)amino}propanoate as obtained in step (g) and 4.14 g of potassium carbonate were suspended in a mixture of 44 mL of acetone and 27 mL of water at 5° C. After stirring at this temperature for 10 minutes, 2.0 g (12 mmol) of hexyl chloroformate were added dropwise. The resulting mixture was stirred at 5° C. for 1 hour. 200 mL of dichloromethane were added to the mixture, which was then heated to 28° C. The organic phase was extracted, washed with 200 mL of brine and dried with anhydrous sodium sulfate. The solvent was removed under vacuum, and the resulting pale yellow oil was dissolved in 10 mL of dichloromethane. Then, a solution of 0.96 g of methanesulfonic acid in 80 mL of acetone at 0° C. was added dropwise over the reaction mixture. The reaction was stirred at room temperature for 1 hour. The resulting solid was isolated by filtration, washed with 40 mL of diethyl ether and dried at 40° C. under vacuum for 5 hours, to yield 4.2 g of dabigatran etexilate mesylate as an off-white solid. Yield: 58.0%. Purity (HPLC, method 1): 98.9%.

Example 3

Synthesis of Dabigatran Etexilate Mesylate a) 4-(Methylamino)-3-nitrobenzoic Acid 400 g (1.98 mol) of 4-chloro-3-nitrobenzoic acid were suspended in 1025 g of a 25-30% aqueous solution of methylamine. After heating to reflux temperature, an orange solution was obtained. The solution was kept at reflux temperature for 4 hours. The solution was cooled to room temperature, and pH was adjusted to about 2 by addition of 2M aqueous sulphuric acid. Precipitation of an orange solid was observed, which was isolated by filtration. The filtered cake was washed with 500 mL of water. The wet solid was mixed with 1.5 L of ethanol and heated to reflux temperature for 1 hour. After cooling to room temperature, the resulting suspension was filtered and the cake was dried at 60° C. under vacuum to obtain 371 g of 4-(methylamino)-3-nitrobenzoic acid as an orange powder. Yield: 95.5%. Purity (HPLC, method 2): 99.4%.

b) Ethyl 3-(2-pyridylamino)propanoate 200 g (2.12 mol) of 2-aminopyridine and 346 mL (3.18 mol) of ethyl acrylate were dissolved in 53 mL of acetic acid. The mixture was heated to 88° C. and stirred overnight at the same temperature. Solvent was removed under vacuum, and the title compound was purified by column chromatography, eluting with ethyl acetate, to obtain 358 g of ethyl 3-(2-pyridylamino)propionate as a pale red solid. Yield: 86.7%.

c) Ethyl 3-{[{1-(methylamino)-2-nitrophen-4-yl}carbonyl](pyridyn-2-yl)amino}propanoate Hydrochloride 95 g (0.48 mol) of 4-(methylamino)-3-nitrobenzoic acid as obtained in step (a) were suspended in a mixture of 172.8 g of thionyl chloride, 1 mL of N,N-dimethylformamide and 480 mL of toluene. The mixture was stirred at reflux temperature for 3 hours. Solvent and excess thionyl chloride were removed by vacuum distillation. The residue was dissolved in 150 mL of toluene, which was subsequently removed by vacuum distillation to remove completely any residual thionyl chloride. This step of dissolving in 150 mL of toluene and removing the solvent by vacuum distillation was repeated. The residue was dissolved in 500 mL of tetrahydrofuran at 5° C. At this point, 150 mL of triethylamine were added to the solution. Then, a solution of 75.2 g (0.39 mol) of ethyl 3-(2-pyridylamino)propanoate as obtained in step (b) in 120 mL of tetrahydrofuran was added dropwise over the reaction mixture. The resulting orange suspension was stirred overnight at room temperature. The solid was filtered and the cake was washed with 150 mL of tetrahydrofuran. The solid was discarded and mother liquors were combined. Solvent was removed by vacuum distillation, and the residue was dissolved in 350 mL of dichloromethane. The resulting solution was washed with 350 mL of water, 350 mL of 2M hydrochloric acid and 350 mL of water. The organic phase was dried with anhydrous sodium sulfate and concentrated under vacuum. The residue was dissolved with 800 mL of ethyl acetate, and dry hydrogen chloride was bubbled into the solution until precipitation was completed. The resulting suspension was stirred at room temperature for 1 hour. The solid was isolated by filtration, washed with 300 mL of ethyl acetate and dried under vacuum to obtain 131.7 g of ethyl 3-{[{1-(methylamino)-2-nitrophen-4-yl}carbonyl](pyridyn-2-yl)amino}propanoate hydrochloride as an orange solid. Yield: 83.2%. Purity (HPLC, method 1): 93.9%.

d) Ethyl 3-{[{2-amino-1-(methylamino)phen-4-yl}carbonyl]pyridyn-2-yl)amino}propanoate (Compound II)

130 g (0.32 mol) of ethyl 3-{[{1-(methylamino)-2-nitrophen-4-yl}carbonyl](pyridyn-2-yl)amino}propanoate hydrochloride as obtained in step (c) were suspended in 1.8 L of ethanol, in the presence of 100 g of ammonium formate and 26 g of a Pd/C catalyst. The reaction mixture was stirred at reflux temperature for 3 hours. After cooling to room temperature, the catalyst was removed by filtration, the filtrate was concentrated under vacuum, and the residue was dissolved in 650 mL of ethyl acetate. The resulting solution was washed with saturated sodium bicarbonate and with water. The organic phase was dried with anhydrous sodium sulfate and was concentrated under vacuum. The residue was dissolved in 110 mL of ethanol and stirred overnight at 0° C. to afford crystallization. The solid was isolated by filtration, washed with 2×30 mL of ethanol and dried at 50° C. under vacuum for 3 hours to yield 33.8 g of ethyl 3-{[{2-amino-1-(methylamino)phen-4-yl}carbonyl](pyridyn-2-yl)amino}propanoate as a brown solid. Yield: 31.0%. Purity (HPLC, method 2): 98.6%.

e) 2-(4-Cyanophenylamino)acetic Acid (Compound III)

77.4 g (0.66 mol) of 4-aminobenzonitrile and 150 g (1.31 mol) of sodium chloroacetate were suspended in 1.1 L of water, and the resulting mixture was stirred at reflux temperature for 6.5 hours. After cooling to 0° C., the resulting suspension was stirred at this temperature overnight. The solid was filtered and washed with 200 mL of water. The resulting solid was suspended in 200 mL of ethyl acetate and stirred at room temperature for 1 hour. The solid was filtered, washed with 200 mL of ethyl acetate and dried at 60° C. under vacuum for 5 hours to yield 85.4 g of 2-(4-cyanophenylamino)acetic acid as an off-white solid. Yield: 74.0%. Purity (HPLC, method 3): 97.8%.

f) Ethyl 3-{[(2-{[(4-cyanophenyl)amino]methyl}-1-methyl-1H-benzimidazol-5-yl)carbonyl](pyridin-2-yl)amino}propanoate Oxalate (Salt of Compound IV)

14.1 g (80 mmol) of 2-(4-cyanophenylamino)acetic acid as obtained in step (e) and 14.2 g (88 mmol) of 1,1'-carbonyldiimidazole were suspended in 600 mL of tetrahydrofuran. The mixture was stirred at reflux temperature for 1 hour. Then, a solution of 25.0 g (73 mmol) of ethyl 3-{[{2-amino-1-(methylamino)phen-4-yl}carbonyl](pyridyn-2-yl)amino}propanoate as obtained in step (d) in 100 mL of tetrahydrofuran was added dropwise over the reaction mixture. The resulting mixture was stirred at reflux temperature for 10 hours, and the solvent was removed by distillation under vacuum. The resulting residue was dissolved in 300 mL of acetic acid and heated to reflux temperature for 1 hour. After cooling to room temperature, solvent was removed by distillation under vacuum. The resulting residue was dissolved in 400 mL of dichloromethane, and the solution was washed with 2×400 mL of water. The organic phase was dried with anhydrous sodium sulfate and the solvent was removed under vacuum. The residue was dissolved in 350 mL of ethyl acetate at 40° C. At this temperature, 12.6 g (0.14 mol) of oxalic acid were added, and the resulting mixture was stirred for 30 minutes at 40° C. After cooling to room temperature, the precipitated solid was isolated by filtration. The solid was stirred with 800 mL of ethanol at reflux temperature for 1 hour. After cooling to room temperature, the solid was isolated by filtration, washed with 50 mL of ethanol and dried at 60° C. under vacuum, to yield 29.8 g of ethyl 3-{[(2-{[(4-cyanophenyl)amino]methyl}-1-methyl-1H-benzimidazol-5-yl)carbonyl](pyridin-2-yl)amino}propanoate oxalate as an off-white solid. Yield: 71.3%. Purity (HPLC, method 1): 97.5%.

g) Ethyl 3-{[(2-{[(4-{carbamimidoyl}phenyl)amino]methyl}-1-methyl-1H-benzimidazol-5-yl)carbonyl](pyridin-2-yl)amino}propanoate (Compound V)

48.9 g (85 mmol) of ethyl 3-{[(2-{[(4-cyanophenyl)amino]methyl}-1-methyl-1H-benzimidazol-5-yl)carbonyl](pyridin-2-yl)amino}propanoate oxalate as obtained in step (f) and 23.8 g of p-toluenesulfonic acid were suspended in 120 mL of a 10M hydrogen chloride solution in ethanol. The mixture was stirred at room temperature for 48 hours. At this point, 200 mL of ethanol were added and the resulting mixture was cooled below 10° C. Ammonia gas was bubbled at this temperature until formation of precipitate was completed. The mixture was stirred at room temperature overnight. Solvent was removed by distillation under vacuum. The residue was dissolved in a mixture of 250 mL of ethanol, 500 mL of water and 7.65 g of sodium hydroxide at 50° C., and was stirred at this temperature for 45 minutes. After cooling to room temperature, the solid was isolated by filtration and washed with 300 mL of water and 200 mL of acetone. Mother liquors were kept, while the solid was stirred with 1 L of methanol at reflux temperature and filtered. The solid was discarded, and the mother liquors were combined. Then, 1 L of ethyl acetate was added dropwise over the solution at room temperature. The precipitated solid was isolated by filtration. The solid was stirred with 100 mL of ethanol at reflux temperature for 1 hour. After cooling to room temperature, the solid was isolated by filtration and dried at 50° C. under vacuum to yield 7.9 g of ethyl 3-{[(2-{[(4-{carbamimidoyl}phenyl)amino]methyl}-1-methyl-1H-benzimidazol-5-yl)carbonyl](pyridin-2-yl)amino}propanoate as a white solid. Yield: 18.5%. Purity (HPLC, method 3): 96.7%.

h) Dabigatran Etexilate Mesylate 4.6 g (9.2 mmol) of ethyl 3-{[(2-{[(4-{carbamimidoyl}phenyl)amino]methyl}-1-methyl-1H-benzimidazol-5-yl)carbonyl](pyridin-2-yl)amino}propanoate as obtained in step (g) and 2.54 g of potassium carbonate were suspended in a mixture of 42 mL of acetone and 25 mL of water at 5° C. After stirring at this temperature for 30 minutes, 1.85 g (11 mmol) of hexyl chloroformate were added dropwise. The resulting mixture was stirred at 5° C. for 1 hour. The suspension was filtered and washed with 2×40 mL of water and 2×40 mL of ethyl acetate. The isolated solid was dissolved in 300 mL of dichloromethane, and the resulting solution was dried with anhydrous sodium sulfate. The solvent was removed under vacuum, and the resulting residue was dissolved in 80 mL of ethyl acetate at reflux temperature. After cooling to 0-5° C., the solid was isolated by filtration and washed with 20 mL of ethyl acetate. The solid was dissolved in 100 mL of acetone at reflux temperature. Then, 1.2 g of methanesulfonic acid was added over the reaction mixture. The reaction was stirred at reflux temperature for 1 hour. After cooling to room temperature, the resulting solid was isolated by filtration, washed with 20 mL of acetone and dried at 50° C. under vacuum for 5 hours, to yield 4.2 g of dabigatran etexilate mesylate as a pale yellow solid. Yield: 63.0%. Purity (HPLC, method 1): 99.1%.

Example 4

Synthesis of Dabigatran Etexilate Mesylate 10.0 g (20 mmol) of ethyl 3-{[(2-{[(4-{carbamimidoyl}phenyl)amino]methyl}-1-methyl-1H-benzimidazol-5-yl)carbonyl](pyridin-2-yl)amino}propanoate as obtained in Example 3, step (g) and 5.6 g of potassium carbonate were suspended in a mixture of 88 mL of acetone and 54 mL of water at 5° C. After stirring at this temperature for 30 minutes, 4.0 g (24 mmol) of hexyl chloroformate were added dropwise. The resulting mixture was stirred at 5° C. for 1 hour. The suspension was filtered and washed with 2×50 mL of water. The mother liquors were extracted with 100 mL of dichloromethane. The organic phase and the filtered solid were combined, and the mixture was heated to achieve complete dissolution of the solid. The solution was dried with anhydrous sodium sulfate. The solvent was removed under vacuum, and the resulting oil was dissolved in 200 mL of acetone at reflux temperature. Then, 2.0 g of methanesulfonic acid was added over the reaction mixture. The reaction was stirred at reflux temperature for 1 hour. After cooling to room temperature, the resulting solid was isolated by filtration, washed with 30 mL of acetone and dried to yield 6.7 g of dabigatran etexilate mesylate as a pale red solid. Yield: 46.2%. Purity (HPLC, method 1): 96.8%. Content of compound (A2) (HPLC, method 1): 1.3%.

The solid was stirred with 500 mL of acetone at reflux temperature for 1 hour. After cooling to 40° C., the solid was isolated by filtration to yield 5.7 g of dabigatran etexilate mesylate. Purity (HPLC, method 1): 97.1%. Content of compound (A2) (HPLC, method 1): 0.9%.

The solid was then stirred with 200 mL of tetrahydrofuran at reflux temperature for 1 hour. After cooling to 40° C., the solid was isolated by filtration and dried to yield 1.7 g of dabigatran etexilate mesylate. Purity (HPLC, method 1): 97.4%. Content of compound (A2) (HPLC, method 1): 0.8%.

Example 5

Synthesis of Dabigatran Etexilate Mesylate

Dabigatran etexilate mesylate as obtained in Example 4 after treatment with acetone and after treatment with tetrahydrofuran were combined with their mother liquors and the resulting mixture was evaporated. The product was combined with 8.0 g of additional dabigatran etexilate mesylate obtained by a similar process and having a total purity (HPLC, method 1) of 97.5% and a content of compound (A2) (HPLC, method 1) of 0.7%. The resulting solid was dissolved in a mixture of 300 mL of dichloromethane and 150 mL of a 5% w/v aqueous potassium carbonate solution. The mixture was stirred at room temperature for 20 minutes. The aqueous phase was discarded, and the organic phase was washed with 2×100 mL of water. The solution was dried with anhydrous sodium sulfate. The solvent was removed under vacuum, and the resulting oil was dissolved in 160 mL of ethyl acetate at reflux temperature. After cooling to 0° C., the resulting suspension was stirred at this temperature overnight, and the solid was isolated by filtration and washed with 20 mL of ethyl acetate. The solid was dried and dissolved in 120 mL of ethyl acetate under heating. After cooling to 0° C., the resulting suspension was stirred at this temperature overnight, and the solid was isolated to yield 7.6 g of dabigatran etexilate.

The solid was dissolved in 200 mL of acetone at reflux temperature. Then, a solution of 1.2 g of methanesulfonic acid in 10 mL of acetone was added dropwise over the reaction mixture. The reaction was stirred at reflux temperature for 1 hour. After cooling to room temperature, the resulting solid was isolated by filtration, washed with 50 mL of acetone and dried to yield 6.5 g of dabigatran etexilate mesylate. Purity (HPLC, method 1): 98.9%. Content of compound (A2) (HPLC, method 1): 0.15%.

Example 6

Synthesis of Dabigatran Etexilate Mesylate a) Ethyl 3-{[{1-(methylamino)-2-nitrophen-4-yl}carbonyl](pyridyn-2-yl)amino}propanoate Hydrochloride 50 g (0.25 mol) of 4-(methylamino)-3-nitrobenzoic acid as obtained in step Example 1, step (a) were suspended in a mixture of 459.2 g of thionyl chloride and 3 mL of N,N-dimethylformamide. The mixture was stirred at reflux temperature for 45 minutes. Excess thionyl chloride was removed by vacuum distillation. The residue was dissolved in 300 mL of toluene, which was subsequently removed by vacuum distillation to remove completely any residual thionyl chloride. This step of dissolving in 300 mL of toluene and removing the solvent by vacuum distillation was repeated. The brownish crystalline residue obtained was dissolved in 280 mL of tetrahydrofuran at 60° C. After cooling to 40° C., 35.1 g of triethylamine were added to the solution. Then, a solution of 45 g (0.23 mol) of ethyl 3-(2-pyridylamino)propanoate as obtained in Example 1, step (b) in 95 mL of tetrahydrofuran was added dropwise over the reaction mixture, keeping the temperature at about 30° C. The resulting mixture was stirred overnight at room temperature. Solvent was removed by vacuum distillation, and the residue was dissolved in 1 L of dichloromethane. The resulting solution was washed with 500 mL of water, 500 mL of 2M hydrochloric acid, 500 mL of saturated sodium bicarbonate and 500 mL of water. The organic phase was dried with anhydrous sodium sulfate and concentrated under vacuum. The residue was dissolved with 600 mL of ethyl acetate, and dry hydrogen chloride was bubbled into the solution until precipitation was completed. The solid was isolated by filtration and dried to obtain 59.7 g of the title compound, which was recrystallized in a mixture of 430 mL of ethanol and 47 mL of acetonitrile at reflux temperature. After cooling to 10° C., solid was isolated by filtration and dried to yield 37.5 g of ethyl 3-{[{1-(methylamino)-2-nitrophen-4-yl}carbonyl](pyridyn-2-yl)amino}propanoate hydrochloride as a yellow solid. Yield: 39.6%. Purity (HPLC, method 1): 97.6%.

b) Ethyl 3-{[{2-amino-1-(methylamino)phen-4-yl}carbonyl](pyridyn-2-yl)amino}propanoate (Compound II)

41.7 g (0.10 mol) of ethyl 3-{[{1-(methylamino)-2-nitrophen-4-yl}carbonyl](pyridyn-2-yl)amino}propanoate hydrochloride as obtained in step (a) were suspended in 500 mL of isopropanol, in the presence of 64.3 g of ammonium formate and 8.8 g of a 5% Pd/C catalyst (55% water content). The reaction mixture was stirred at reflux temperature for 2.5 hours. After cooling to room temperature, the catalyst was removed by filtration, the filtrate was concentrated under vacuum, and the residue was dissolved in 700 mL of ethyl acetate. The resulting solution was washed with 200 mL of saturated sodium bicarbonate and with 400 mL of water. The organic phase was dried with anhydrous sodium sulfate and was concentrated under vacuum to yield 24.9 g of ethyl 3-{[{2-amino-1-(methylamino)phen-4-yl}carbonyl](pyridyn-2-yl)amino}propanoate as a dark oil. Yield: 71.3%. Purity (HPLC, method 2): 89.2%.

c) 2-(4-Cyanophenylamino)acetic Acid (Compound III)

54.0 g (0.46 mol) of 4-aminobenzonitrile and 107.2 g (0.92 mol) of sodium chloroacetate were suspended in 730 mL of water, and the resulting mixture was stirred at reflux temperature for 4 hours. After cooling to room temperature, pH was adjusted to 8-9 with sodium bicarbonate. The resulting solution was washed with 2×200 mL of ethyl acetate, and 5M hydrochloric acid was added to the aqueous phase until pH=3. The precipitated solid was isolated by filtration, washed with 100 mL of water and dried to yield 57.1 g of 2-(4-cyanophenylamino)acetic acid as an off-white solid. Yield: 70.9%. Purity (HPLC, method 3): 92.9%.

d) Ethyl 3-{[(2-{[(4-cyanophenyl)amino]methyl}-1-methyl-1H-benzimidazol-5-yl)carbonyl](pyridin-2-yl)amino}propanoate Oxalate (Salt of Compound IV)

13.6 g (77 mmol) of 2-(4-cyanophenylamino)acetic acid as obtained in step (c) and 12.7 g (78 mmol) of 1,1'-carbonyldiimidazole were suspended in 400 mL of tetrahydrofuran. The mixture was stirred at reflux temperature for 1 hour. Then, a solution of 24.9 g (73 mmol) of ethyl 3-{[{2-amino-1-(methylamino)phen-4-yl}carbonyl](pyridyn-2-yl)amino}propanoate as obtained in step (b) in 100 mL of tetrahydrofuran was added dropwise over the reaction mixture. The resulting mixture was stirred overnight at reflux temperature, and the solvent was removed by distillation under vacuum. The resulting residue was dissolved in 270 mL of acetic acid and heated to reflux temperature for 1 hour. After cooling to room temperature, solvent was removed by distillation under vacuum. The resulting residue was dissolved in 250 mL of ethyl acetate, and the solution was washed with 250 mL of water. The organic phase was dried with anhydrous sodium sulfate and heated to 50-60° C. At this temperature, 8.8 g (98 mmol) of oxalic acid were added, and the resulting mixture was stirred for 1 hour at 50-60° C. After cooling to room temperature, the precipitated solid was filtered and dried under vacuum, to yield 23.5 g of ethyl 3-{[(2-{[(4-cyanophenyl)amino]methyl}-1-methyl-1H-benzimidazol-5-yl)carbonyl](pyridin-2-yl)amino}propanoate oxalate as a brownish solid. Yield: 56.4%. Purity (HPLC, method 1): 83% e) Ethyl 3-{[(2-{[(4-{carbamimidoyl}phenyl)amino]methyl}-1-methyl-1H-benzimidazol-5-yl)carbonyl](pyridin-2-yl)amino}propanoate (Compound V)

23.3 g (41 mmol) of ethyl 3-{[(2-{[(4-cyanophenyl)amino]methyl}-1-methyl-1H-benzimidazol-5-yl)carbonyl](pyridin-2-yl)amino}propanoate oxalate as obtained in step (d) and 10.6 g of p-toluenesulfonic acid were suspended in 69.4 g of a 10M hydrogen chloride solution in ethanol. The mixture was stirred at room temperature for 24 hours. At this point, 200 mL of ethanol were added and the resulting mixture was cooled to 0° C. Ammonia gas was bubbled at this temperature until formation of precipitate was completed. The mixture was stirred at 10° C. for 2 hours, and then was stirred at room temperature overnight. Solvent was removed by distillation under vacuum. The residue was dissolved in a mixture of 40 mL of ethanol, 40 mL of water and 0.11 g of sodium hydroxide at 55° C., and was stirred at this temperature for 45 minutes. After cooling to 10° C., the mixture was stirred at this temperature for 1 hour. The solid was removed by filtration and discarded. The mother liquors were concentrated under vacuum to remove ethanol. The precipitated solid was isolated by filtration, washed with 100 mL of water and with 2×50 mL of acetone, to yield 14.0 g of ethyl 3-{[(2-{[(4-{carbamimidoyl}phenyl)amino]methyl}-1-methyl-1H-benzimidazol-5-yl)carbonyl](pyridin-2-yl)amino}propanoate as an off-white solid. Yield: 68.9%. Purity (HPLC, method 3): 79.3%.

f) Dabigatran Etexilate 14.0 g (28 mmol) of ethyl 3-{[(2-{[(4-{carbamimidoyl}phenyl)amino]methyl}-1-methyl-1H-benzimidazol-5-yl)carbonyl](pyridin-2-yl)amino}propanoate as obtained in step (e) and 12.4 g of potassium carbonate were suspended in a mixture of 140 mL of water and 700 mL of tetrahydrofuran. After stirring at room temperature for 15 minutes, 4.6 g (28 mmol) of hexyl chloroformate were added dropwise. The resulting mixture was stirred at room temperature for 1 hour. The organic phase was extracted, washed with 200 mL of brine and dried with anhydrous sodium sulfate. The solvent was removed under vacuum, and the resulting solid was suspended in 100 mL of ethyl acetate at 10° C. The solid was isolated by filtration and purified by column chromatography eluting with ethyl acetate, to yield 7.6 g of dabigatran etexilate as an off-white solid. Yield: 43.2%. Purity (HPLC, method 1): 98.3%.

g) Dabigatran Etexilate Mesylate 7.6 g (12 mmol) of dabigatran etexilate as obtained in step (f) were suspended in 600 mL of ethyl acetate. The mixture was heated to 45° C., and 1.15 g of methanesulfonic acid were added over the reaction mixture. The reaction was stirred at this temperature for 1 hour. After cooling to room temperature and stirring at this temperature for 1 hour, the resulting solid was isolated by filtration, and washed with 120 mL of ethyl acetate and 120 mL of diethyl ether to yield 7.8 g of dabigatran etexilate mesylate as a pale yellow solid. Yield: 89.0%. Purity (HPLC, method 1): 99.3%.

Example 7

Accelerated Stability Study of Dabigatran Etexilate Mesylate

Dabigatran etexilate mesylate as obtained in Example 6 was stored in a double polyethylene bag and stored at 40° C. and 75% relative humidity for 3 months.

Example 8

Impurity Contents

Dabigatran etexilate mesylate as obtained in Examples 2, 3, 5 and 7 was analyzed by HPLC (method 1) to quantify contents of compounds (A1), (A2), (B1), (B2), (B3), (B4), (C1), (C2), (C3), (D) in these samples, see Table 1. Impurity contents are expressed in area % with respect to dabigatran etexilate.

| Compound Identity | Compound/Impurity contents (area %) | | | |
|---|---|---|---|---|
| | Example 2 | Example 3 | Example 5 | Example 7 |
| (A1) | 0.15 | 0.42 | 0.24 | 0.38 |
| (A2) | 0.65 | 0.10 | 0.15 | 0.42 |
| (B1) | 0.16 | 0.11 | 0.13 | 3.8 |
| (B2) | 0.01 | — | — | 0.25 |
| (B3) | 0.19 | 0.14 | 0.16 | 7.62 |
| (B4) | 0.08 | 0.03 | 0.38 | 0.71 |
| (C1) | — | — | — | 1.64 |
| (C2) | 0.06 | 0.06 | 0.07 | 1.57 |
| (C3) | 0.06 | 0.04 | 0.06 | 0.32 |
| (D) | 0.04 | 0.03 | 0.06 | 0.18 |

Example 9

Isolation of Ethyl 2-{[(4-{[(hexyloxy)carbonyl]carbamimidoyl}phenyl)amino]methyl}-1-methyl-1H-benzimidazol-5-carboxylate (Compound (A2))

10.0 g (16 mmol) of crude ethyl 3-{[(2-{[(4-{carbamimidoyl}phenyl)amino]methyl}-1-methyl-1H-benzimidazol-5-yl)carbonyl](pyridin-2-yl)amino}propanoate (HPLC purity, method 3: 82.1%) as obtained in Example 2, step (g), was suspended in a mixture of 7.07 g (51 mmol) of potassium carbonate, 42.7 mL of water and 427 mL of tetrahydrofuran. The mixture was stirred at room temperature for 30 minutes. After cooling to 15° C., 2.81 g (17 mmol) of hexyl chloroformate were added while keeping the reaction temperature between 15 to 20° C. The resulting mixture was stirred at room temperature for 2 hours. The mixture was filtered and the solid was discarded. The organic phase was extracted from the mother liquors, and the solvent was removed by vacuum distillation. The residue was dissolved in 200 mL of dichloromethane, and residual aqueous phase was extracted. The organic phase was dried with anhydrous sodium sulfate. The solvent was removed under vacuum to yield 11.0 g of crude dabigatran etexilate as a red slurry. Purity (HPLC, method 1): 87.3%. Content of compound (A2) (HPLC, method 1): 9.8%.

4.0 g of the crude dabigatran etexilate containing 9.8% of compound (A2) was purified by column chromatography (60-100 mesh silica gel), eluting with a gradient from ethyl acetate:methanol (3:1 v/v) mixture to ethyl acetate:methanol (1:1 v/v). After solvent evaporation of the selected fractions containing pure ethyl 2-{[(4-{[(hexyloxy)carbonyl]carbamimidoyl}phenyl)amino]methyl}-1-methyl-1H-benzimidazol-5-carboxylate (compound (A2)), 0.3 g of the title compound were obtained.

Example 10

Synthesis of 3-{[(2-{[(4-{[({hexyloxy}carbonyl)amino]carbonyl}phenyl)-amino]methyl}-1-methyl-1H-benzimidazol-5-yl)carbonyl](pyridin-2-yl)amino}propanoic Acid (Compound (B1))

25 g of dabigatran etexilate mesylate were suspended in 180 mL of deionized water. 1.32 g of methanesulfonic acid were added. The reaction mixture was heated to 55° C. and stirred at this temperature for 7 days. The resulting mixture was filtered, and the solid was dried under vacuum. The solid was purified by column chromatography, eluting with dichloromethane:methanol (10:1 v/v) mixture. After solvent evaporation of the selected fractions containing the desired compound, 5.9 g of 3-{[(2-{[(4-{[({hexyloxy}carbonyl)amino]carbonyl}phenyl)-amino]methyl}-1-methyl-1H-benzimidazol-5-yl)carbonyl](pyridin-2-yl)amino}propanoic acid were obtained.

Example 11

Synthesis of Ethyl 3-{[(2-{[(4-{[({hexyloxy}carbonyl)amino]carbonyl}-phenyl)amino]methyl}-1-methyl-1H-benzimidazol-5-yl)carbonyl](pyridin-2-yl)amino}propanoate (Compound (B3))

32 g of dabigatran etexilate were suspended in 320 mL of deionized water. 5.4 g of methanesulfonic acid were added. The reaction mixture was heated to 50° C. and stirred at this temperature for 72 hours. The resulting mixture was filtered, and the solid was dried under vacuum. The solid was purified by column chromatography, eluting with ethyl acetate:methanol (15:1 v/v) mixture. After solvent evaporation of the selected fractions containing the desired compound, 15 g of ethyl 3-{[(2-{[(4-{[({hexyloxy}carbonyl)amino]carbonyl}-phenyl)amino]methyl}-1-methyl-1H-benzimidazol-5-yl)carbonyl](pyridin-2-yl)amino}propanoate were obtained.

Particular embodiments of the invention are described below:

Embodiment 1

A compound of formula (A)

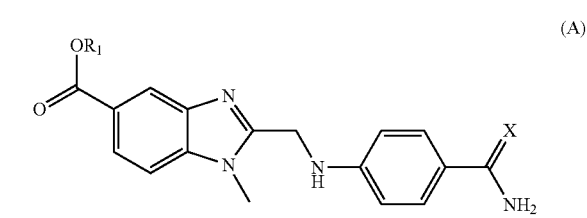

(A)

wherein R1 represents C1-4 alkyl, and X represents either NH, or N(C=O)O(CH2)5CH3.

Embodiment 2

A compound (A1) having the chemical name ethyl 2-{[(4-{carbamimidoyl}phenyl)amino]methyl}-1-methyl-1H-benzimidazol-5-carboxylate and structure

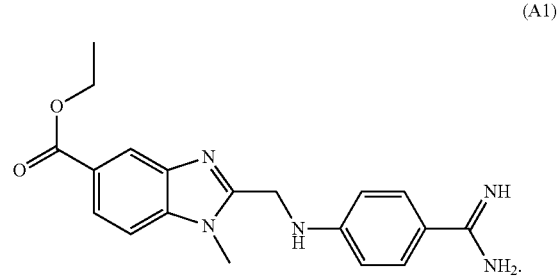 [SMILES: CCOC(=O)c1ccc2c(c1)nc(CNc1ccc(C(=N)N)cc1)n2C]

(A1)

Embodiment 3

A compound (A2) having the chemical name ethyl 2-{[(4-{[(hexyloxy)carbonyl]carbamimidoyl}phenyl)amino]methyl}-1-methyl-1H-benzimidazol-5-carboxylate and structure

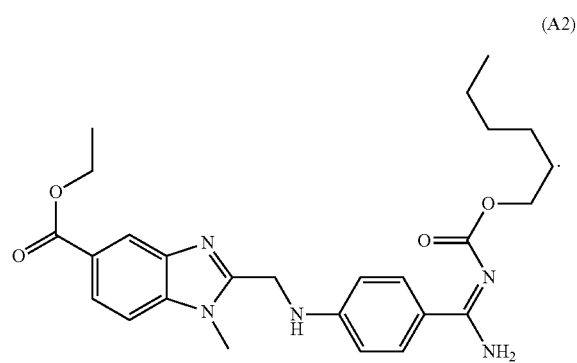 [SMILES: CCCCCCOC(=O)/N=C(/N)c1ccc(NCc2nc3cc(C(=O)OCC)ccc3n2C)cc1]

(A2)

Embodiment 4

A compound of formula (B)

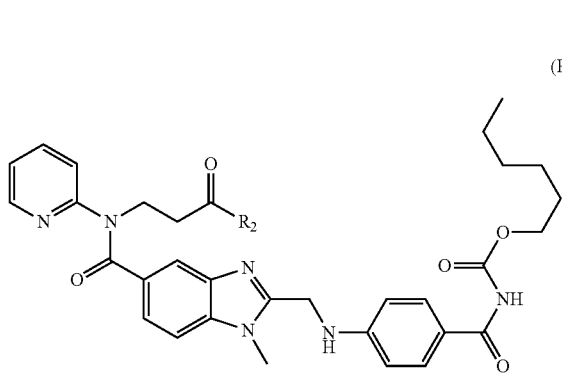
(B)

wherein R₂ represents hydroxyl, $C_{1-4}$ alkoxy or $NH_2$.

Embodiment 5

A compound (B1) having the chemical name 3-{[(2-{[(4-{[({hexyloxy}carbonyl)amino]carbonyl}phenyl)amino]methyl}-1-methyl-1H-benzimidazol-5-yl)carbonyl](pyridin-2-yl)amino}propanoic acid and structure

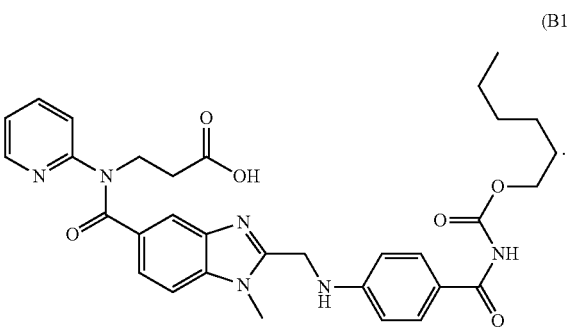
(B1)

Embodiment 6

A compound (B2) having the chemical name methyl 3-{[(2-{[(4-{[({hexyloxy}carbonyl)amino]carbonyl}phenyl)amino]methyl}-1-methyl-1H-benzimidazol-5-yl)carbonyl](pyridin-2-yl)amino}propanoate and structure

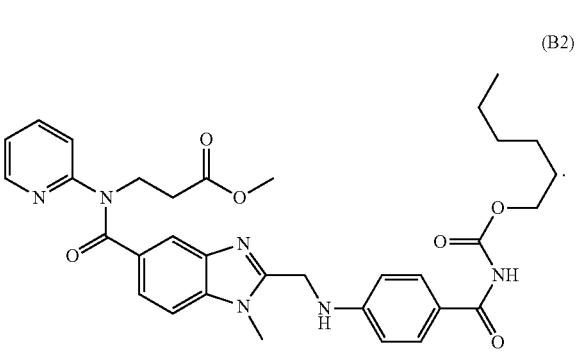 [SMILES: CCCCCCOC(=O)NC(=O)c1ccc(NCc2nc3cc(C(=O)N(CCC(=O)OC)c4ccccn4)ccc3n2C)cc1]
(B2)

Embodiment 7

A compound (B3) having the chemical name ethyl 3-{[(2-{[(4-{[({hexyloxy}carbonyl)amino]carbonyl}phenyl)amino]methyl}-1-methyl-1H-benzimidazol-5-yl)carbonyl](pyridin-2-yl)amino}propanoate and structure

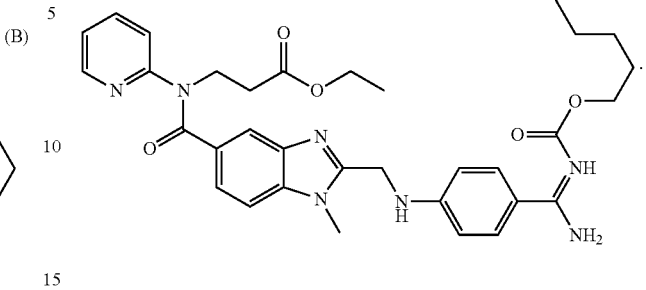
(B3)

Embodiment 8

A compound (B4) having the chemical name 3-{[(2-{[(4-{[(hexyloxy)carbonyl]carbamimidoyl}phenyl)amino]methyl}-1-methyl-1H-benzimidazol-5-yl)carbonyl](pyridin-2-yl)amino}propanamide and structure

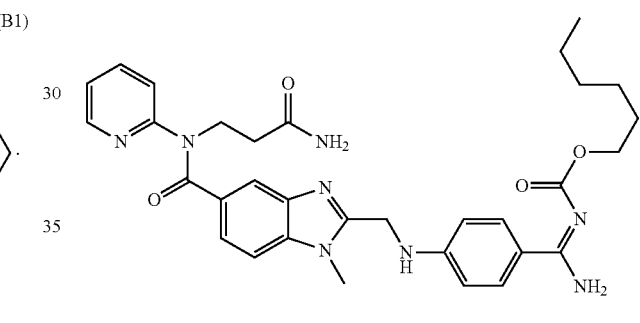
(B4)

Embodiment 9

A compound according to anyone of embodiments 1 to 8, in isolated form.

Embodiment 10

A compound according to embodiment 9, which is in substantially pure form.

Embodiment 11

A compound according to embodiments 9 or 10, having a purity of greater than about 90%.

Embodiment 12

A compound according to anyone of embodiments 1 to 11, or one or more of the following compounds:

(i) Compound (C1) having the chemical name 3-{[(2-{[(4-{carbamimidoyl}phenyl)amino]methyl}-1-methyl-1H-benzimidazol-5-yl)carbonyl](pyridin-2-yl)amino}propanoic acid and structure (C1)

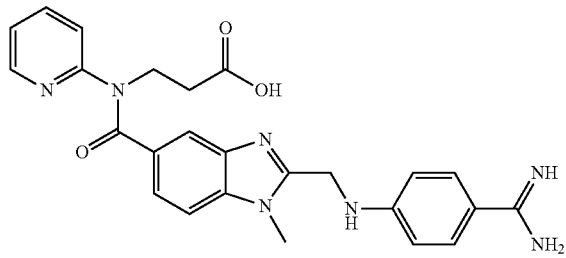

(ii) Compound (C2) having the chemical name 3-{[(2-{[(4-{[(hexyloxy)carbonyl]carbamimidoyl}phenyl)amino]methyl}-1-methyl-1H-benzimidazol-5-yl)carbonyl](pyridin-2-yl)amino}propanoic acid and structure (C2)

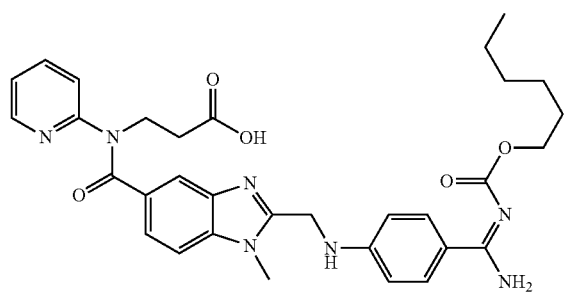

(iii) Compound (C3) having the chemical name methyl 3-{[(2-{[(4-{[(hexyloxy)carbonyl]carbamimidoyl}phenyl)amino]methyl}-1-methyl-1H-benzimidazol-5-yl)carbonyl](pyridin-2-yl)amino}propanoate and structure (C3)

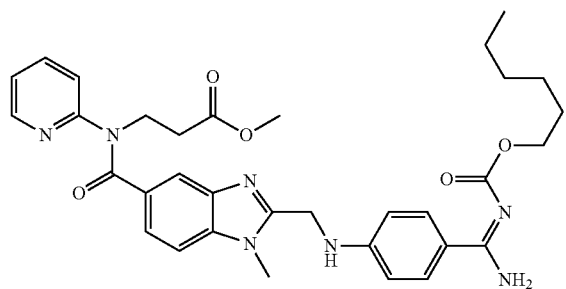

(iv) Compound (D) having the chemical name 4-{[(hexyloxy)carbonyl]carbamimidoyl}aniline and structure (D)

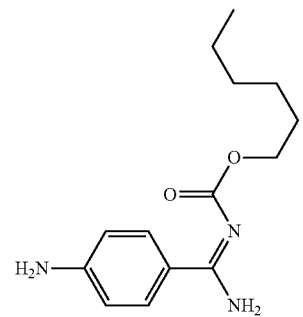

for use as a reference marker or reference standard to analyze the purity of dabigatran etexilate and/or its salts, and/or its solvates.

Embodiment 13

Use of one or more of compounds of formulae (A) to (D) according to embodiment 12, as a reference marker to analyze the purity of dabigatran etexilate and/or its salts, and/or its solvates.

Embodiment 14

Use of one or more of compounds of formulae (A) to (D) according to embodiment 12, as a reference standard to quantify the amount of one or more of compounds of formulae (A) to (D) in a sample of dabigatran etexilate and/or its salts, and/or its solvates.

Embodiment 15

A method of testing the purity of a sample of dabigatran etexilate and/or its salts, and/or its solvates, which method comprises assaying the sample for the presence of one or more of compounds of formulae (A) to (D) according to embodiment 12, by using a reference marker or reference standard according to any of embodiments 12 to 14.

Embodiment 16

A chromatographic method for testing the purity of a sample of dabigatran etexilate and/or its salts, and/or its solvates, by determining the presence of one or more of compounds of formulae (A) to (D) according to embodiment 12 in said sample comprising dabigatran etexilate, said method comprising:

(a) dissolving a sample of dabigatran etexilate and/or its salts, and/or its solvates, in a solvent to produce a sample solution;

(b) dissolving a sample of any one or more of compounds of formulae (A) to (D) in a solvent to produce a reference marker solution;

(c) subjecting the sample solution and the reference marker solution to a chromatographic technique; and (d) determining the presence of any one or more of compounds of formulae (A) to (D) in the sample by reference to the presence of one or more of compounds of formulae (A) to (D) present in the reference marker solution.

Embodiment 17

A method according to embodiment 16, wherein the chromatographic method is HPLC.

Embodiment 18

A method for analyzing the amount of one or more of compounds of formulae (A) to (D) according to embodiment 12 present in a sample of dabigatran etexilate and/or its salts, and/or its solvates, using analytical HPLC, said method comprising:

(a) measuring by HPLC the area under the peak corresponding to one or more of compounds of formulae (A) to (D) in a sample of dabigatran etexilate and/or its salts, and/or its solvates, having an unknown amount of one or more of compounds of formulae (A) to (D);

(b) measuring by HPLC the area under the peak corresponding to one or more of compounds of formulae (A) to (D) in a reference standard having a known amount of said one or more compounds of formulae (A) to (D); and (c) determining the amount of said one or more compounds of formulae (A) to (D) in the sample of dabigatran etexilate and/or its salts, and/or its solvates, by comparing the area calculated in step (a) with the area calculated in step (b).

Embodiment 19

A method according to embodiment 18, for analyzing the purity of a sample of dabigatran etexilate and/or its salts, and/or its solvates.

Embodiment 20

Use according to embodiments 13 or 14, or a method according to anyone of embodiments 15 to 19, wherein said sample of dabigatran comprises, or is derived from, any of the following:

(a) dabigatran etexilate API; or (b) a pharmaceutical composition comprising dabigatran etexilate; or (c) a dabigatran etexilate salt or solvate; or (d) a pharmaceutical composition comprising a dabigatran etexilate salt or solvate.

Embodiment 21

Use according to embodiment 13, 14 or 20, or a method according to anyone of embodiments 15 to 20, wherein said compound of formulae (A) to (D) is compound (B3).

Embodiment 22

Dabigatran etexilate and/or its salts, and/or its solvates, which has been subjected to a method according to anyone of embodiments 15 to 21.

Embodiment 23

Dabigatran etexilate and/or its salts, and/or its solvates, which includes pharmaceutically acceptable amounts of one or more of said compounds of formulae (A) to (D) according to embodiment 12.

Embodiment 24

Dabigatran etexilate and/or its salts, and/or its solvates, substantially free of one or more of said compounds of formulae (A) to (D) according to embodiment 12.

Embodiment 25

Dabigatran etexilate according to embodiment 24, which comprises less than about 5% of one or more of said compounds of formulae (A) to (D) according to embodiment 12 as measured by HPLC.

Embodiment 26

Dabigatran etexilate mesylate according to anyone of embodiments 22 to 25, wherein said compound of formulae (A) to (D) according to embodiment 12 is compound (B3).

Embodiment 27

A pharmaceutical composition comprising dabigatran etexilate according to anyone of embodiments 22 to 26.

Embodiment 28

A pharmaceutical composition comprising dabigatran etexilate mesylate, which on storage for at least three months at 40° C. and 75% relative humidity, includes less than about 10% of compound (B3), relative to dabigatran etexilate.

Embodiment 29

A pharmaceutical composition according to embodiment 28, which includes less than about 9% of compound (B3), relative to dabigatran etexilate.

Embodiment 30

A pharmaceutical composition according to embodiment 29, which includes less than about 8% of compound (B3), relative to dabigatran etexilate.

Embodiment 31

A pharmaceutical composition according to embodiment 30, which includes compound (B3) in an amount of about 7.55 to 7.70%, relative to dabigatran etexilate.

Embodiment 32

A process of preparing dabigatran etexilate and/or its salts, and/or its solvates, wherein one or more of compounds of formulae (A) to (D) according to embodiment 12 forms in said process.

Embodiment 33

A process according to embodiment 32, which further comprises testing the purity of dabigatran etexilate and/or its salts, and/or its solvates, according to embodiments 15 or 16.

Embodiment 34

A process of preparing dabigatran etexilate mesylate, which process comprises the following synthetic steps:

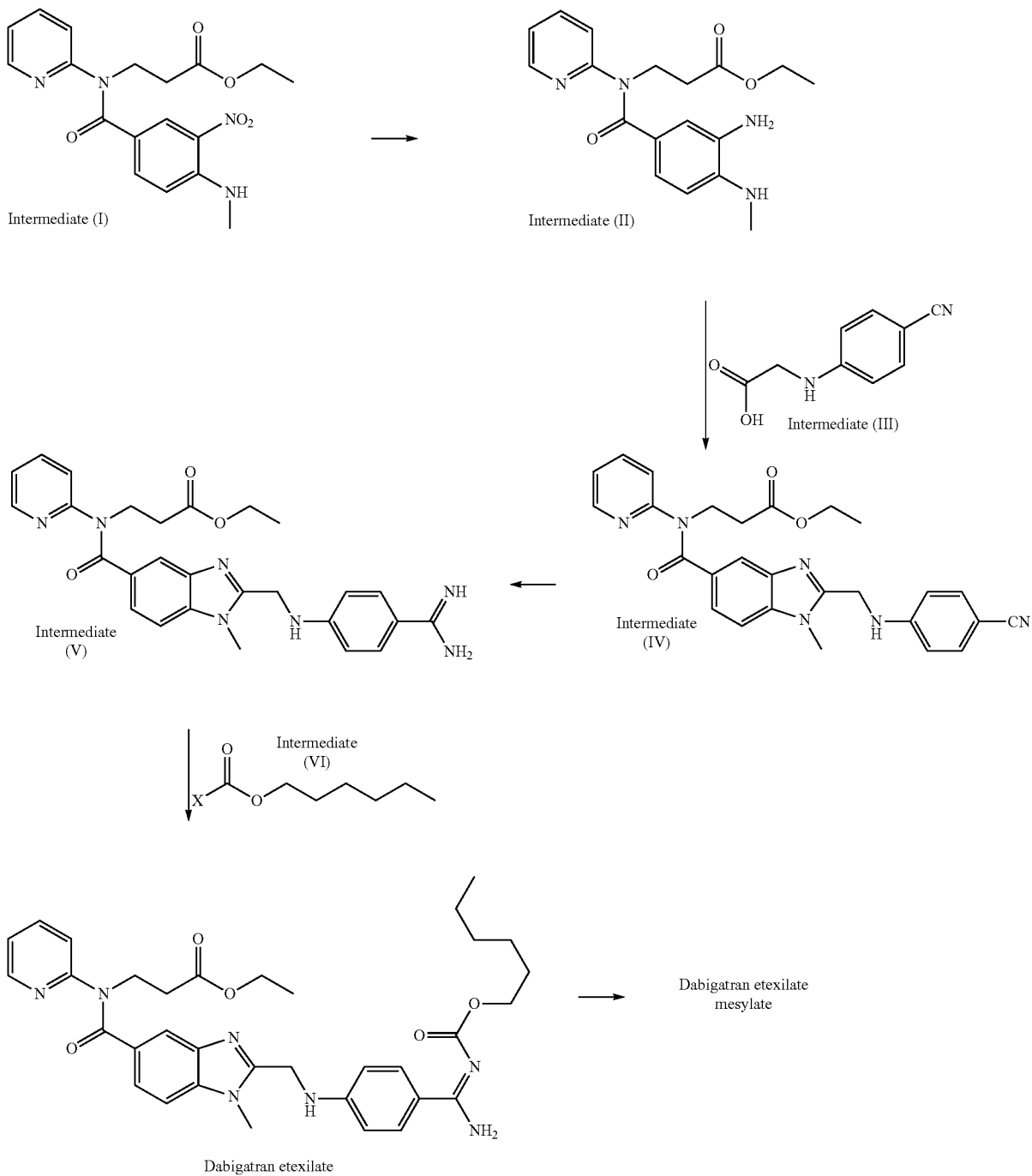

wherein X is a leaving group.

Embodiment 35

A process according to embodiment 34, which prepares dabigatran etexilate mesylate according to anyone of embodiments 22 to 26.

Embodiment 36

A process according to embodiments 34 or 35, wherein said intermediate (I) above is isolated as a hydrochloride salt; and/or said intermediate (V) is isolated as the free base; and/or said intermediate (I) is prepared as a hydrochloride salt, by the following intermediate steps.

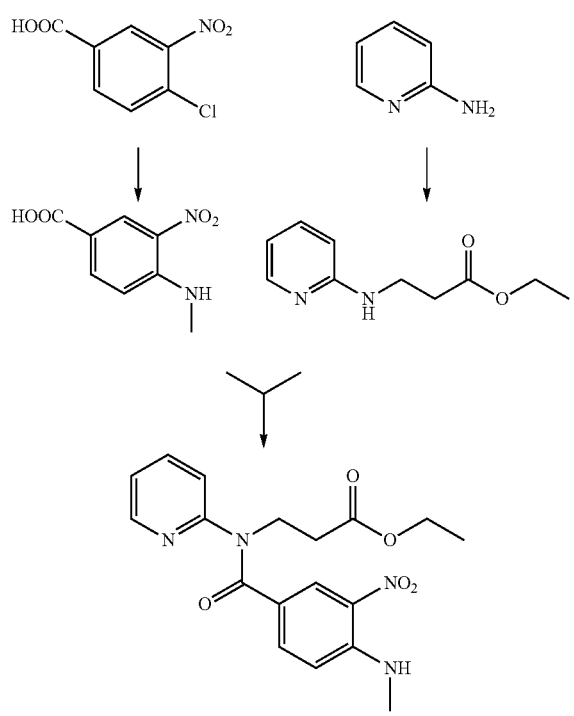

Embodiment 37

A chromatographic method for testing the purity of a sample of dabigatran etexilate and/or its salts (for example the mesylate salt (1:1)), and/or its solvates (for example hydrates), by determining the presence of one or more of compounds of formulae (A) to (D) in a sample comprising dabigatran etexilate and/or its salts or solvates as above, said method comprising:

(a) dissolving a sample of dabigatran etexilate and/or its salts (for example the mesylate salt (1:1)), and/or its solvates (for example hydrates), in a solvent to produce a sample solution;

(b) dissolving a sample of one or more of compounds of formulae (A) to (D) in a solvent to produce a reference marker solution;

(c) subjecting the sample solution and the reference marker solution to a chromatographic technique; and (d) determining in the sample of dabigatran etexilate and/or its salts the presence of one or more of compounds of formulae (A) to (D) in the sample by reference to the presence of one or more of compounds of formulae (A) to (D) present in the reference marker solution.

Embodiment 38

A method according to embodiment 37 wherein the determination of the presence of one or more compounds of formula (A) to (D) in the sample of dabigatran etexilate and/or its salts is effected by comparing the retention (retention time in HPLC, retention factor in TLC) of the different components of the sample of dabigatran etexilate and/or its salts separated by said chromatographic method with the retention of the compounds of formulae (A) to (D) under the same chromatographic conditions (stationary phase, mobile phase, temperature and pressure).

All references, including publications, patent applications, and patents, cited herein are hereby incorporated by reference to the same extent as if each reference were individually and specifically indicated to be incorporated by reference and were set forth in its entirety herein.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A compound of formula (B)

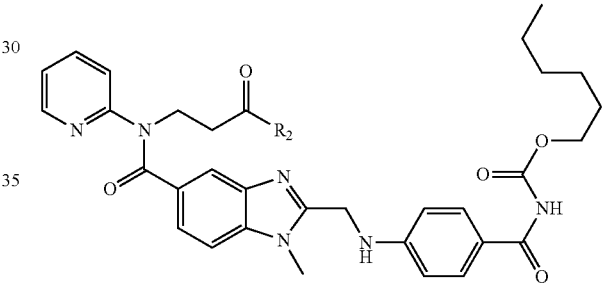

(B)

wherein $R_2$ is hydroxyl, $C_{1-4}$ alkoxy, or $NH_2$.

2. A compound (B1) according to claim 1, wherein $R_2$ is a hydroxyl group.

3. A compound (B) according to claim 1, wherein $R_2$ is $C_{1-4}$ alkoxy.

4. A compound (B2) according to claim 3, wherein the $C_{1-4}$ alkoxy is a methoxy group.

5. A compound (B3) according to claim 3, wherein the $C_{1-4}$ alkoxy is an ethoxy group.

6. A compound (B4) according to claim 1, wherein $R_2$ is a $NH_2$ group.

7. A compound according to claim 1 in isolated form.

8. A method for analyzing the purity of dabigatran etexilate or a salt or solvate thereof in a sample comprising determining the amount present in the sample of one or more of compounds of formula (B).

9. A method according to claim 8, wherein the dabigatran etexilate or a salt or solvate in the sample is derived from one or more sources selected from the group consisting of dabigatran etexilate active pharmaceutical ingredient, a pharmaceutical composition comprising dabigatran etexilate, dabigatran etexilate salt or solvate thereof, and a pharmaceutical composition comprising dabigatran etexilate salt or solvate thereof.

10. The method of claim 8, wherein the purity of dabigatran etexilate or a salt or solvate thereof is analyzed by determining the amount of compound (B3) present in the sample.

11. A method for determining the presence of one or more compounds of formulae (B) in a sample comprising dabigatran etexilate or a salt or solvate thereof, said method comprising:
(a) providing a sample solution comprising dabigatran etexilate or a salt or solvate thereof;
(b) providing a reference marker solution comprising one or more compounds of formulae (B); and
(c) subjecting the sample solution and the reference marker solution to chromatographic conditions to obtain a retention factor of the components of the sample solution and of the components of the reference marker solution; and
(d) comparing the retention factor of the components of the sample solution with the retention factor of the components of the reference marker solution.

12. The method of claim 11, wherein the dabigatran etexilate salt is dabigatran etexilate mesylate.

13. The method of claim 12, wherein the chromatographic conditions are the same for the sample solution and the reference marker solution.

14. The method of claim 11 further comprising quantifying the amount of one or more compounds of formulae (B) present in the sample solution.

15. A method for preparing dabigatran etexilate, or a salt or solvate thereof, suitable for pharmaceutical use comprising:
(a) providing dabigatran etexilate, or a salt or solvate thereof;
(b) assessing the purity of said dabigatran etexilate, or a salt or solvate thereof, using the method of claim 14; and
optionally subjecting the dabigatran etexilate, or a salt or solvate thereof, to one or more purification steps.

16. The method according to claim 15 comprising:
(a) providing dabigatran etexilate, or a salt or solvate thereof;
(b) assessing the purity of said dabigatran etexilate, or a salt or solvate thereof;
(c) subjecting the dabigatran etexilate, or a salt or solvate thereof, to a purification step; and
(d) optionally, repeating steps (b) and (c) one or more times.

17. The method according to claim 16, wherein said compound of formulae (B) in step (b) is a compound of formula (B1).

18. The method according to claim 16, wherein said compound of formulae (B) in step (b) is a compound of formula (B3).

* * * * *